US012677871B2

(12) United States Patent
Jackson

(10) Patent No.: US 12,677,871 B2
(45) Date of Patent: Jul. 14, 2026

(54) MONOLITHIC MICROFABRICATED VIBRATING MESH ATOMIZER

(71) Applicant: UNM Rainforest Innovations, Albuquerque, NM (US)

(72) Inventor: Nathan Morrow Jackson, Rio Rancho, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 1098 days.

(21) Appl. No.: 17/428,430

(22) PCT Filed: Feb. 7, 2020

(86) PCT No.: PCT/US2020/017154
§ 371 (c)(1),
(2) Date: Aug. 4, 2021

(87) PCT Pub. No.: WO2020/163680
PCT Pub. Date: Aug. 13, 2020

(65) Prior Publication Data
US 2022/0104544 A1 Apr. 7, 2022

Related U.S. Application Data

(60) Provisional application No. 62/803,114, filed on Feb. 8, 2019, provisional application No. 62/803,102, filed on Feb. 8, 2019.

(51) Int. Cl.
*A24F 40/05* (2020.01)
*A24F 40/10* (2020.01)
(Continued)

(52) U.S. Cl.
CPC ............. *A24F 40/05* (2020.01); *A24F 40/10* (2020.01); *A24F 40/485* (2020.01); *A24F 40/51* (2020.01);
(Continued)

(58) Field of Classification Search
CPC ................................................ B05B 17/0646
See application file for complete search history.

(56) References Cited

U.S. PATENT DOCUMENTS 4,850,534 A 7/1989 Takahashi et al.
4,996,080 A 2/1991 Daraktchiev
(Continued)

FOREIGN PATENT DOCUMENTS

EP 0546964 A1 6/1993
EP 1022063 A1 7/2000
(Continued)

OTHER PUBLICATIONS

"International Application Serial No. PCT/US2020/017154, International Preliminary Report on Patentability mailed Aug. 19, 2021", 6 pgs.

(Continued)

*Primary Examiner* — Bradley H Philips
(74) *Attorney, Agent, or Firm* — Schwegman, Lundberg & Woessner, P.A.

(57) ABSTRACT

In various embodiments, an apparatus can comprise one or more integrated mesh membranes operable to vibrate based on an integrated structure with a piezoelectric material. The integrated mesh membrane can be implemented in an atomizer, which can be constructed as a monolithic vibrating mesh atomizer. A portable vibrating mesh atomizer can be implemented in a number of applications including, but not limited to, a vaping device or portable liquid medicine delivery system. Additional apparatus, systems, and methods are disclosed.

37 Claims, 16 Drawing Sheets

(51) Int. Cl.

| | | |
|---|---|---|
| *A24F 40/485* | (2020.01) | |
| *A24F 40/51* | (2020.01) | |
| *A24F 40/70* | (2020.01) | |
| *A61M 11/00* | (2006.01) | |
| *B05B 17/00* | (2006.01) | |
| *B05B 17/06* | (2006.01) | |

(52) U.S. Cl.
CPC ........... *A24F 40/70* (2020.01); *A61M 11/005* (2013.01); *B05B 17/0607* (2013.01); *B05B 17/0646* (2013.01); *A61M 2205/0233* (2013.01); *A61M 2205/0294* (2013.01); *A61M 2207/00* (2013.01)

(56) References Cited

U.S. PATENT DOCUMENTS

| | | | | |
|---|---|---|---|---|
| 5,152,456 | A | 10/1992 | Ross et al. | |
| 5,591,490 | A | 1/1997 | Quate | |
| 6,235,177 | B1 | 5/2001 | Borland et al. | |
| 7,226,151 | B2 | 6/2007 | Murai | |
| 11,813,618 | B2 | 11/2023 | Jackson et al. | |
| 2001/0013554 | A1* | 8/2001 | Borland | B41J 2/1631 |
| | | | | 239/5 |
| 2003/0112300 | A1 | 6/2003 | Chung et al. | |
| 2003/0178507 | A1* | 9/2003 | Maria Rijn Van | B01D 61/18 |
| | | | | 239/337 |
| 2004/0256487 | A1* | 12/2004 | Collins, Jr. | A61M 11/005 |
| | | | | 239/338 |
| 2010/0003499 | A1 | 1/2010 | Krogman et al. | |
| 2013/0120505 | A1 | 5/2013 | Nystrom et al. | |
| 2017/0119059 | A1 | 5/2017 | Zuber et al. | |
| 2017/0319796 | A1* | 11/2017 | Germinario | A61M 15/025 |
| 2018/0161525 | A1 | 6/2018 | Liu et al. | |
| 2019/0014819 | A1* | 1/2019 | Sur | B05B 17/0646 |
| 2020/0290077 | A1 | 9/2020 | Jackson et al. | |

FOREIGN PATENT DOCUMENTS

| | | | | | |
|---|---|---|---|---|---|
| EP | 1813428 | B1 | 3/2011 | | |
| EP | 2886185 | A1 | 6/2015 | | |
| JP | H0780369 | B2 | 8/1995 | | |
| JP | 2002318193 | A | 10/2002 | | |
| JP | 2004190537 | A | 7/2004 | | |
| KR | 20170129349 | A | 11/2017 | | |
| WO | WO-0176762 | A2 | 10/2001 | | |
| WO | WO-2008029216 | A1 | 3/2008 | | |
| WO | WO-2011154394 | A1 | 12/2011 | | |
| WO | WO-2016150715 | A1 | 9/2016 | | |
| WO | WO-2017149165 | A1 * | 9/2017 | .......... | A61M 11/005 |
| WO | WO-2020163680 | A1 | 8/2020 | | |

OTHER PUBLICATIONS

Sharma, Pallavi, et al., "Spin-Spray Deposition of Spin on Glass Using MEMS Atomizer", IEEE MEMS Virtual Conference, (2021), 681-364.

"International Application Serial No. PCT/US2020/017154, International Search Report mailed May 28, 2020", 3 pgs.
"International Application Serial No. PCT/US2020/017154, Written Opinion mailed May 28, 2020", 4 pgs.
U.S. Appl. No. 17/569,093, filed Jan. 5, 2022, Spin-Spray Deposition Using Vibrating Mesh Atomizer.
"U.S. Appl. No. 17/569,093, Final Office Action mailed Jan. 6, 2025", 10 pgs.
"U.S. Appl. No. 17/569,093, Non Final Office Action mailed Jul. 11, 2024", 10 pgs.
"U.S. Appl. No. 17/569,093, Response filed Jun. 13, 2024 to Restriction Requirement mailed May 3, 2024", 5 pgs.
"U.S. Appl. No. 17/569,093, Response filed Sep. 27, 2024 to Non Final Office Action mailed Jul. 11, 2024", 10 pgs.
"U.S. Appl. No. 17/569,093, Restriction Requirement mailed May 3, 2024", 7 pgs.
Murata, K., et al., "e-Print and Printable Electronics", (Jul./Aug. 2011), 74-78.
"U.S. Appl. No. 17/569,093, Non Final Office Action mailed Apr. 4, 2025", 11 pgs.
"U.S. Appl. No. 17/569,093, Response filed Mar. 5, 2025 to Final Office Action mailed Jan. 6, 2025", 12 pgs.
"Magnetic Thin Film Characterization by Spin Spray Process", A Thesis Presented by Ogheneyunume Ighogbedhe Obi to the Department of Electrical and Computer Engineering for the degree of Master of Science in Electrical Engineering in the field of Electronic Circuits, Semiconductor Devices and Microfabrication, (Nov. 2008), 75 pgs.
Caruntu, et al., "Magnetic characterization of nanocrystalline nickel ferrite films processed by a spin-spraying method", Journal of Physics D Applied Physics 38 811, (2005), 6 pgs.
Ergul, Adem B, "Nano Circuits Based on Vertical Transport", Royal Institute of Technology Master of Science Thesis, (Dec. 2005), 44 pgs.
Kim, Hyungmo, et al., "Laser interference lithography using spray/spin photoresist development method for consistent periodic nanostructures", Current Applied Physics 14 (2014) 209e214, (2014), 6 pgs.
Okazaki, Takuya, et al., "Spectroelectrochemical Evaluation of a ZnO Optically Transparent Electrode Prepared by the Spin-spray Technique", Electroanalysis 2020, 32, 1681-1688, (2020), 8 pgs.
Olszewski, Oskar Z, et al., "A silicon-based MEMS vibrating mesh nebulizer for inhaled drug delivery", Procedia Engineering 168 (2016) 1521-1524, (2016), 4 pgs.
Packeer, F, "Alternative Spin-On-Glass (SOG) material characterization for Deep-Submicron (<0.35 um) soft reflow fabrication process", IOP Conf. Series: Materials Science and Engineering 380, (2018), 8 pgs.
Peterson, Reuben, "Literature Review of Spin on Glass", Los Alamos National Laboratory, (Mar. 2, 2016), 9 pgs.
Pham, Nga, et al., "Spin, Spray coating and Electrodeposition of photoresist for MEMS structures—A comparison", (Mar. 2003), 7 pgs.
"U.S. Appl. No. 17/569,093, Response filed Jul. 2, 2025 to Non Final Office Action mailed Apr. 4, 2025", 10 pgs.
"U.S. Appl. No. 17/569,093, Final Office Action mailed Oct. 14, 2025", 12 pgs.

* cited by examiner

100

107

103

105

108

106

707-1

49.61 μM 27.76 μM 9.910 μM 707-2

36.83 μM

CLOSE TO MEMBRANE CENTER

INHALE: W1

2.739 μM 807-1

INLET

OUTLET

INLET

LIQUID

OUTLET 807-2

FUNCTIONAL GROUP

HEADGROUP

R    R    R    R    R    R

R

R

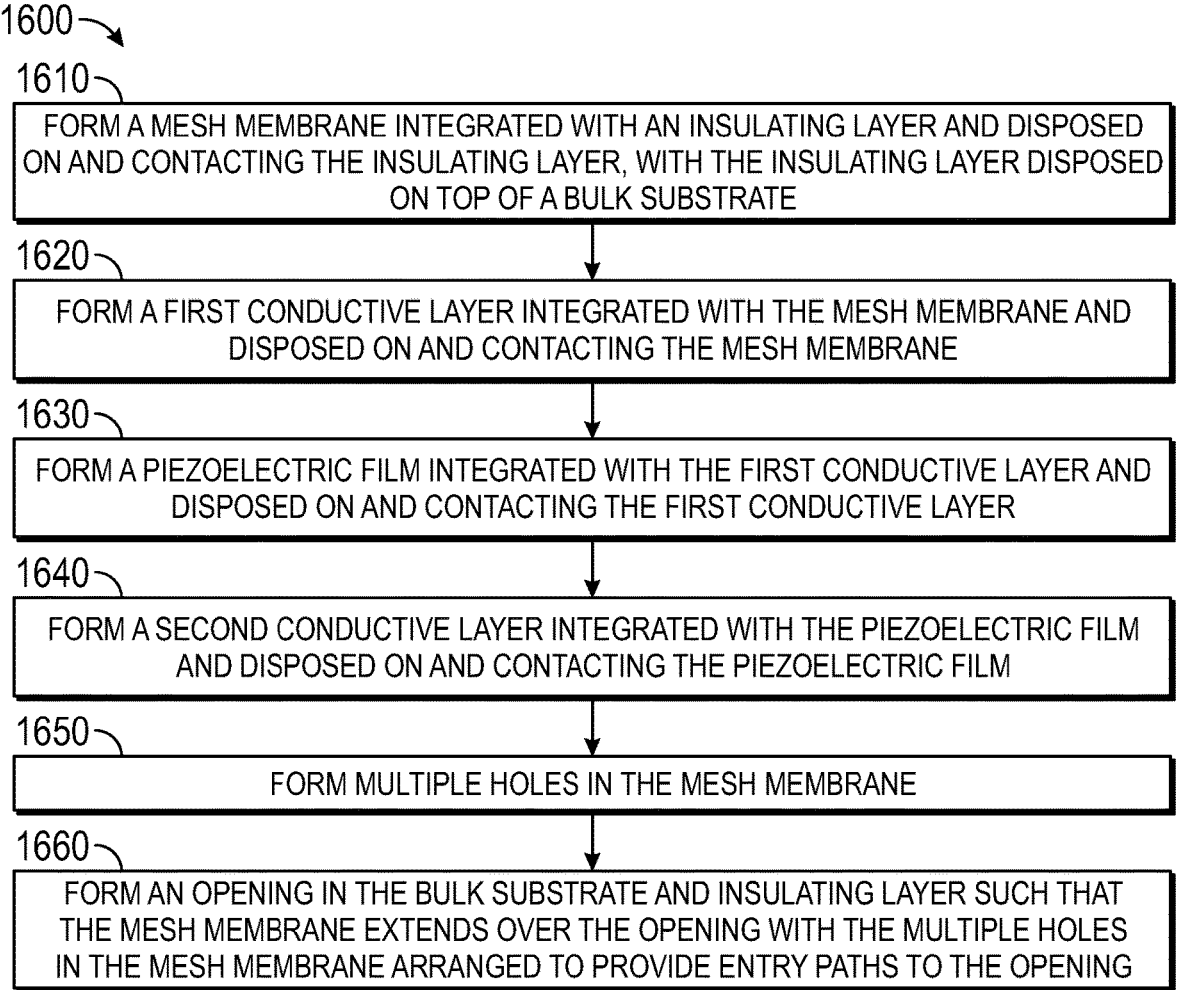

1600

1610

FORM A MESH MEMBRANE INTEGRATED WITH AN INSULATING LAYER AND DISPOSED ON AND CONTACTING THE INSULATING LAYER, WITH THE INSULATING LAYER DISPOSED ON TOP OF A BULK SUBSTRATE

1620

FORM A FIRST CONDUCTIVE LAYER INTEGRATED WITH THE MESH MEMBRANE AND DISPOSED ON AND CONTACTING THE MESH MEMBRANE

1630

FORM A PIEZOELECTRIC FILM INTEGRATED WITH THE FIRST CONDUCTIVE LAYER AND DISPOSED ON AND CONTACTING THE FIRST CONDUCTIVE LAYER

1640

FORM A SECOND CONDUCTIVE LAYER INTEGRATED WITH THE PIEZOELECTRIC FILM AND DISPOSED ON AND CONTACTING THE PIEZOELECTRIC FILM

1650

FORM MULTIPLE HOLES IN THE MESH MEMBRANE

1660

FORM AN OPENING IN THE BULK SUBSTRATE AND INSULATING LAYER SUCH THAT THE MESH MEMBRANE EXTENDS OVER THE OPENING WITH THE MULTIPLE HOLES IN THE MESH MEMBRANE ARRANGED TO PROVIDE ENTRY PATHS TO THE OPENING

FIG. 16

MONOLITHIC MICROFABRICATED VIBRATING MESH ATOMIZER

CLAIM OF PRIORITY

This application is a U.S. National Stage Filing under 35 U.S.C. 371 from International Application No. PCT/US2020/017154, filed 7 Feb. 2020, and published as WO 2020/163680 on 13 Aug. 2020, which application claims the priority benefit of U.S. Provisional Application Ser. No. 62/803,102, filed 8 Feb. 2019, entitled "MONOLITHIC MICROFABRICATED PIEZOMEMS ATOMIZER" and the priority benefit of U.S. Provisional Application Ser. No. 62/803,114, filed 8 Feb. 2019, entitled "PORTABLE VIBRATING MESH ATOMIZER," which applications are incorporated herein by reference in their entirety.

BACKGROUND

Atomizers or aerosol generators are widely used in various applications ranging from respiratory drug therapy to fuel injection, additive manufacturing, spray coatings, neonatal humidifiers, pesticides and many other applications. Atomizers are devices that emit micro-droplets or ultrafine spray of liquid from a bulk liquid source. During atomization process the liquid is in contact with a mesh membrane which is excited into mechanical vibration by a piezoelectric actuator. During the mechanical vibration the liquid is pumped or extruded through a plurality of holes or apertures in the mesh and is output on the other side of the mesh as an aerosol or droplets of the liquid. Alternative methods of atomization can be achieved through a vibrating horn, using acoustic resonators such as surface acoustic wave resonators, or by traditional methods using air pressure (jet) or ultrasound.

Current vibrating mesh atomizers are assembled by bonding multiple components using standard manufacturing capabilities to create a complete device. Components include holders, washers, piezoelectric rings to cause the vibration, membranes with apertures, and bonding adhesives. The membranes are fabricated using laser drilling or electroforming techniques, and typically consist of metal or polymer membranes. These devices use bulk commercial components such as piezoelectric actuators, and the entire devices need to be assembled using standard manufacturing practices.

Conventional assembly of these devices has used various bulk components, such as a piezoelectric ring of lead zirconate titanate (PZT), which leads to added cost and low yield. A prior monolithic vibrating mesh was based on silicon substrate and uses standard pyramidal shape holes or apertures, which can lead to undesired stress due to the sharp corners. Such structures have been designed specifically for nebulizers, which use low viscosity fluids.

Current vaping atomizers used in electronic cigarettes (e-cigarettes) and medicinal inhaled drug delivery use heat to vaporize liquid into an aerosol, which produces undesired ultrafine particles. Vaping devices include, in addition to e-cigarettes, vape pens, advanced personal vaporizers, and other similar devices. Current portable vaping atomizers use a conducting coil which, when a voltage/current is applied, heats up depending on the amount of current used. The heat causes the liquid to atomize. The liquids used in electronic cigarettes usually consist of propylene glycol or vegetable glycerin, nicotine and various flavoring agents. When these get heated, they produce nanoparticles, and undesired byproducts due to the heating, which may pose significant health risks. Therefore, there is a demand to develop an alternative method of generating aerosols for these applications.

BRIEF DESCRIPTION OF THE DRAWINGS

Embodiments of the invention are illustrated by way of example and not limitation in the figures of the accompanying drawings in which:

FIG. 16 is a flow diagram of features of an example method of forming an apparatus having a mesh membrane, in accordance with various embodiments.

DETAILED DESCRIPTION

Figure 1A:
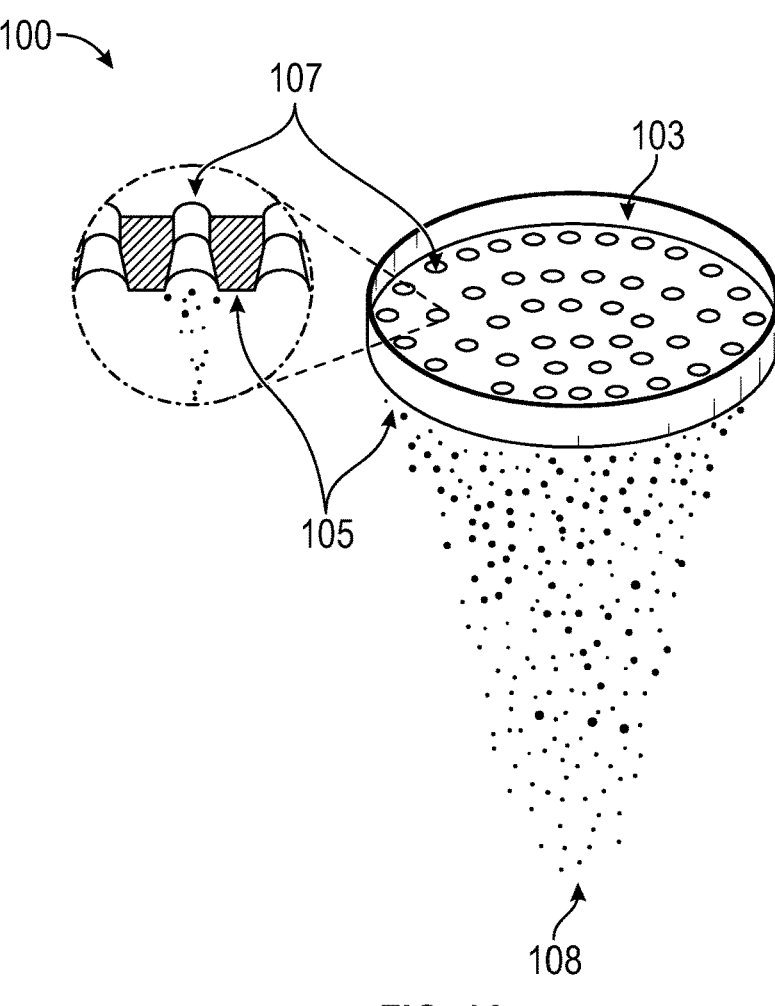
FIGS. 1A-1C are illustrations of examples of a vibrating mesh, a silicon mesh with an integrated piezoelectric actuator, and a microfabricated silicon mesh generating aerosol, in accordance with various embodiments.

The following detailed description refers to the accompanying drawings that show, by way of illustration and not limitation, various example embodiments of the invention. These embodiments are described in sufficient detail to enable those skilled in the art to practice these and other embodiments. In order to avoid obscuring embodiments of the invention, some well-known system configurations and process steps are not disclosed in detail. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

Current atomizer and aerosol generator technology is typically based on air pressure or ultrasound to break up liquid and force it out of a baffle to filter micro-droplet sizes. However, implementation of such technology produces a wide range of droplet sizes, which is not desired in most applications. A vibrating mesh technology was previously developed that combines a nozzle and atomizer into one device, which was able create a uniform droplet size and is primarily used in the nebulizer industry. However, implementation of this technology uses bulk machining and manufacturing techniques and requires assembly of multiple components including mesh membrane, piezoelectric ring, washers, adhesives etc. This leads to low yield and high cost, where using electroforming techniques for manufacturing leads to poor hole reliability and non-repeatable hole dimensions. The manufacturing process also limits the shape and size of the holes and pitch, which limits the flow rate. In addition, the manufacturing process prevents the device from altering the droplet size performance by not allowing certain modifications, such as change in hole dimensions to sub-micron hole size, reduced pitch size, integration of microfluidic chambers, surface topography alterations, hydrophobicity alterations, specialty coatings, integration of sensors and electronics and use of various materials for the membrane substrate and piezoelectric materials. A discussion of monolithic integrated mesh devices for fluid dispensers can be found in WO2017/149165, which is incorporated by reference herein in its entirety.

In various embodiments, structures can be fabricated to enhance droplet performance for various liquid viscosities. Polymer substrates can be used in manufacturing low frequency mesh devices. In addition, unique hole designs can be manufactured by combining various etch techniques, such as anisotropic, isotropic and wet and dry etching techniques such as reactive ion etching, deep reactive ion etching, wet chemical etching, and XeF2 etching. Also, methods of integrating microfluidic chambers can be implemented to dispense various liquids. Microfluidic chambers can be added using standard photolithography using epoxy, resist, SU-8, dry film, or 3D printed technology. These methods can be used to create single or multiple chambers of fluids to dispense single liquids or combination of liquids at any given point.

In various embodiments as taught herein, microfabrication techniques are used to monolithically manufacture vibrating mesh devices with integrated thin film piezoelectric materials. Manufacturing vibrating mesh devices can include, but is not limited to, vibrating mesh devices that combine nozzle and atomizer into one device. Such microfabrication techniques allows one to make modifications to address the abovementioned issues to control droplet size uniformity and flow rate. The piezoelectric materials can be an integral component of a micro-electro-mechanical systems (MEMS) device. Such a MEMS device can be referred to as a piezoMEMS device.

In various embodiments, fabrication techniques for unique hole designs and shapes can include altering etching processes in a substrate, where the substrate can be selected from various substrates from silicon, glass, ceramics, or polymers. Fabrication methods can include integrating thin film piezoelectrics and methods of creating a reservoir with microfluidic chambers to dispense multiple liquids within a single device. Hydrophobicity of the surface of nozzle holes of a mesh can be altered, which allows for higher viscosity liquids to be dispensed. The hydrophobicity can be altered through surface chemistry or by coating monolayers or functional groups to the surface of the nozzle by various techniques such as reactive ion etching, plasma chemical vapor deposition or wet chemistry techniques. The abovementioned alterations can affect the droplet size, droplet shape, flow rate, and reliability of the liquid. Droplet size and shape is also dependent on viscosity of the liquid and force required to squeeze liquid through the holes. These alterations allow high viscosity liquids to be implemented. In addition, specialty coatings can be deposited on the surface of the membrane and nozzle to prevent liquid to membrane surface interaction. Such coatings can include but are not limited to coatings of Parylene™. The specialty coatings can prevent contamination issues and help prevent clogging of the nozzle.

In various embodiments, methods of fabricating a vibrating mesh device can include use of a silicon substrate and/or a polymer substrate. For a silicon substrate of a vibrating mesh device, a silicon wafer or silicon on insulator wafer can be used for this process. The process involves deposition or growth of insulating material followed by the deposition of a conductive film such as a metal film, deposition of a piezoelectric material, and deposition of another conductive film, which can be another metal film. The films can be deposited or grown using various microfabrication techniques such as physical vapor deposition, sputtering, chemical vapor deposition, spin coating, bonding, or epitaxial grown films. The conductive films and piezoelectric films can be patterned and etched to the silicon substrate, where the silicon substrate can act as the mesh membrane. Holes for the mesh membrane can be etched using various techniques. Etching techniques can include anisotropic wet etching, dry plasma based anisotropic etching using reactive ion etch, dry plasma based anisotropic etching using deep reactive ion etch, dry isotropic etching, or wet isotropic etching. The wet etching can use potassium hydroxide (KOH), tetramethylammonium hydroxide (TMAH), ethylene diamine pyrochatechol (EDP), hydrofluoric/nitric/acetic acid (HNA), or other suitable etching compound. Using these methods and combining methods can allow one to create unique hole shapes such as a pyramidal, hourglass, wine glass, and cylindrical shapes, as well as straight or tapered hole shapes.

For a polymer substrate of a vibrating mesh device, using a silicon wafer, polymers can be deposited through spin coating or chemical vapor deposition. A photosensitive polymer, such as SU-8, can be deposited with thicknesses in the range of 1-700 μm. Using advanced grayscale lithography techniques, unique hourglass hole shapes can be patterned using special grayscale masks and using UV exposure. The photosensitive polymer can either act as the membrane material or it could act as a master mold to create new polymer membranes using soft-lithography techniques, which could include polymer or elastomer membranes. Piezoelectric material can either be deposited onto the polymer substrate or it can be deposited prior to depositing and patterning the polymer. Piezoelectric nanoparticles can be incorporated into the polymer substrate to create an all-in-one hybrid material. This unique method allows one to make vibrating mesh devices using a polymer substrate, which lowers the stiffness of the device, allowing for higher displacement, lower frequency, and reduced cost.

In both cases of silicon and polymer substrates, surface hydrophobicity of the holes can be modified by attaching monolayers to make the surface more hydrophilic or more hydrophobic. Materials with a special affinity for water are known as hydrophilic, such as materials for which water can spread across, maximizing contact. Materials that naturally repel water, causing droplets to form, are known as hydrophobic. In both cases of silicon and polymer substrates, monolayers can be applied using surface plasma techniques, wet chemical, or atomic layer deposition. The hydrophobicity affects the droplet size, droplet shape, and the force required to push liquid out of a hole of a mesh. Functional groups, such as $OH^-$ groups, can be used to make a surface more hydrophilic, while fluorine-based groups can be used to make a surface more hydrophobic.

An associated reservoir or microfluidic chamber can be monolithically fabricated using thick polymer films, such as but not limited to SU-8, which can be patterned on the membrane using spin coating and lithography techniques to create individual chambers that allow different liquids to be dispensed at once. Different size droplets can be dispensed by varying the shape of the holes within that particular chamber.

Figure 1B:
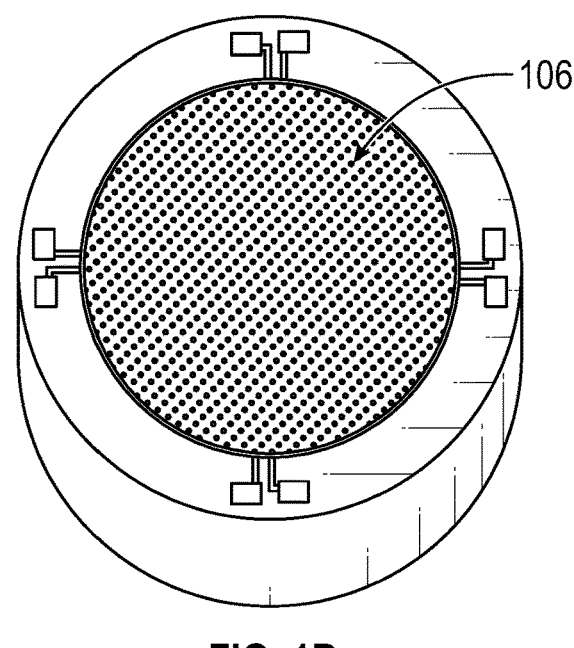
Figure 1C:
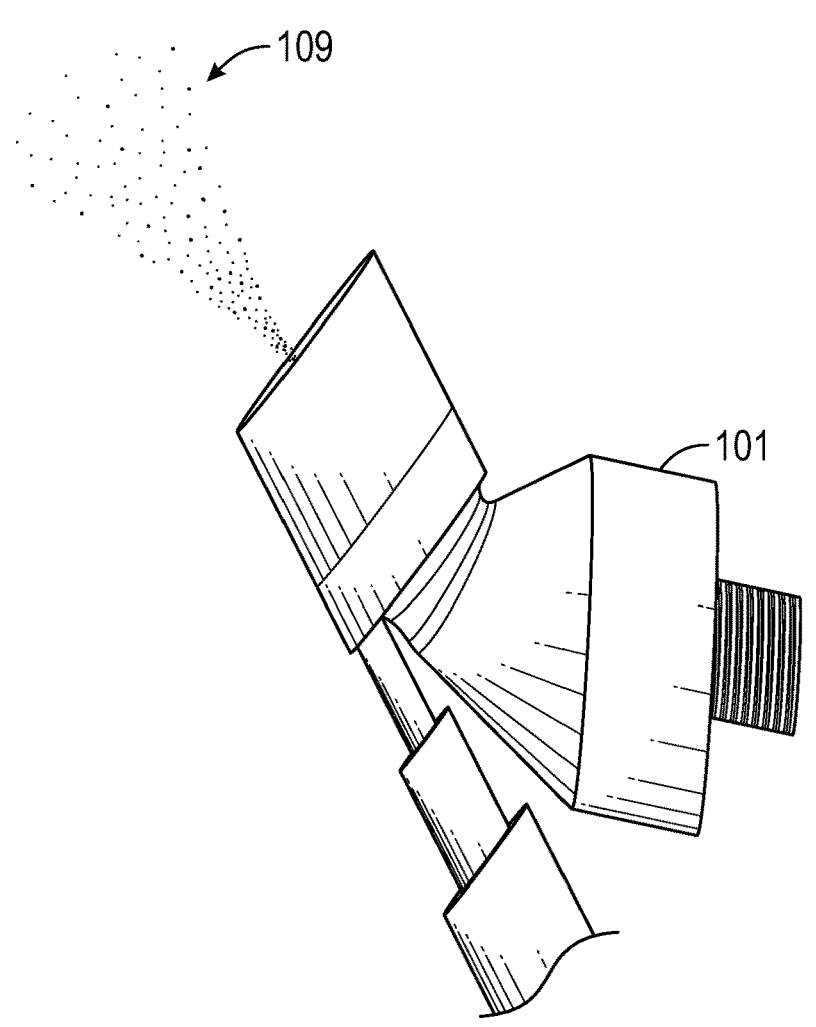

FIGS. 1A-1C are illustrations of examples of a vibrating mesh, a silicon mesh with an integrated piezoelectric actuator, and a microfabricated silicon mesh generating aerosol. FIG. 1A shows an embodiment of an example vibrating mesh 100 in which liquid medicine 103 can be applied to holes 107 in the vibrating membrane 105, providing an aerosol/mist 108. FIG. 1B shows an embodiment of an example silicon mesh with an integrated piezoelectric actuator having a piezoelectric membrane 106. FIG. 1C shows an embodiment of an example microfabricated silicon mesh 101 generating aerosol providing micro-droplets 109.

Figure 2:
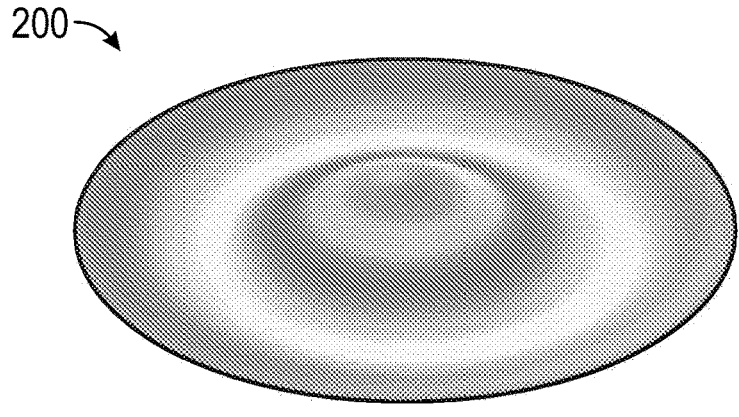
FIG. 2 illustrates a mode of operation using finite element modelling, in accordance with various embodiments.

FIG. 2 illustrates a mode of operation using finite element modelling (FEM). Shown is a FEM model of an integrated mesh device for atomization of a fluid or liquid, where the integrated mesh device includes a silicon membrane with a thin film of piezoelectric material deposited on top. The mode of operation shown is for a 02 resonant mode.

Figure 3A:
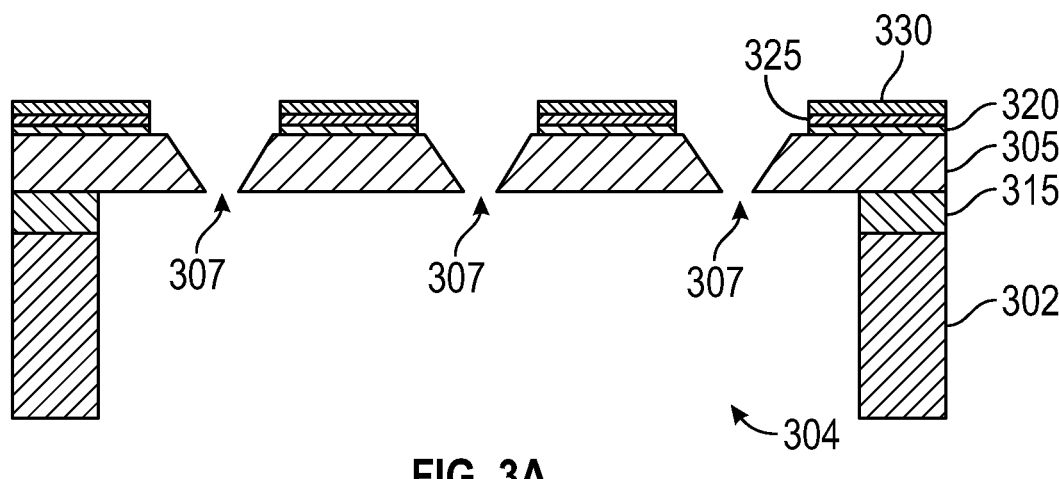
FIG. 3A shows a cross-section of an example vibrating mesh membrane with integrated piezoelectric film, in accordance with various embodiments.

FIG. 3A shows a cross-section of an embodiment of an example vibrating mesh membrane 305 with integrated piezoelectric film 325. Vibrating mesh membrane 305 can be a silicon vibrating mesh membrane, though other materials can be used such as, but not limited to one or more polymers. Vibrating mesh membrane 305 is disposed above a substrate 302, separated from substrate 302 by an electrically insulating region 315. Electrically insulating region 315 can be an oxide or other dielectric material. The oxide can be, but is not limited to, silicon oxide. A first electrode 320 is disposed on vibrating mesh membrane 305 with piezoelectric film 325 disposed on the first electrode 320. A second electrode 330 is located on piezoelectric film 325. Though not shown, a protective layer can cover the second electrode 330. In processing to construct this structure, a portion of substrate 302 and electrically insulating region 315 has been removed, providing an opening 304. At a number of locations along a stack, defined by vibrating mesh membrane 305, first electrode 320, piezoelectric film 325, and second electrode 330, holes 307 are provided to opening 304. A signal can be applied between first electrode 320 and second electrode 330 actuating piezoelectric film 325 to move, causing vibrating mesh membrane 305 to vibrate.

Figure 3B:
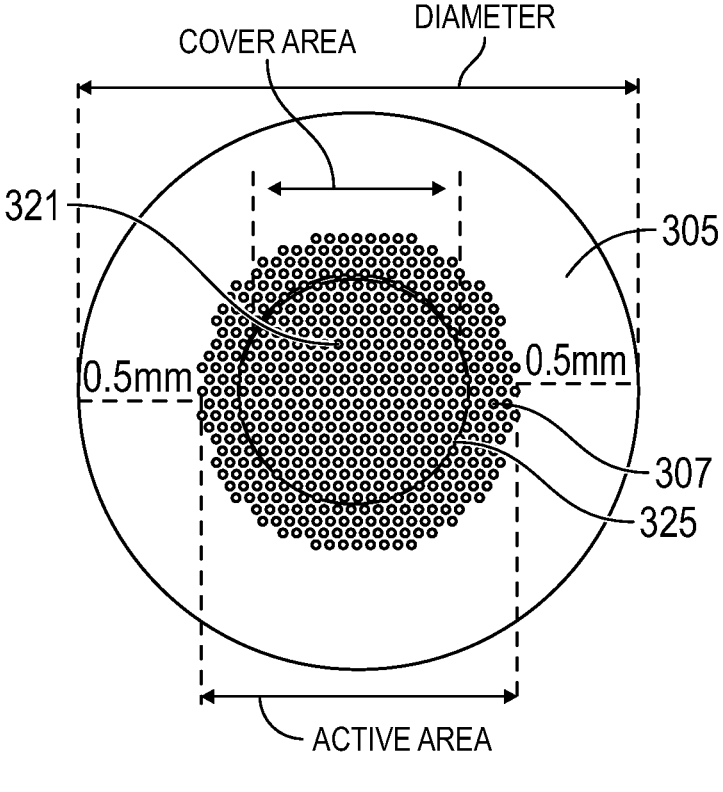
FIG. 3B is a top view of the structure of FIG. 3A, in accordance with various embodiments.

FIG. 3B is a top view of the structure of FIG. 3A. This top view shows a diameter of an active area of the structure and mesh membrane 305 with its multiple holes 307. A stack 321 including first electrode 320, piezoelectric film 325, and second electrode 330 is also indicated. FIGS. 3A and 3B show piezoelectric film 325, first electrode 320, and second electrode 330 on mesh membrane 305, where the structure uses the vertical displacement mode of the piezoelectric material of piezoelectric film 325 to cause vertical displacement of the membrane. The piezoelectric material can be any piezoelectric material that is conducive to integrated fabrication process, the design of the structure, and the application for which mesh membrane 305 is being used. Likewise, first electrode 320 and second electrode 330 can be any conducive material that can be used as an electrical contact and is conducive to integrated fabrication process, the design of the structure, and the application for which mesh membrane 305 is being used.

Figure 4A:
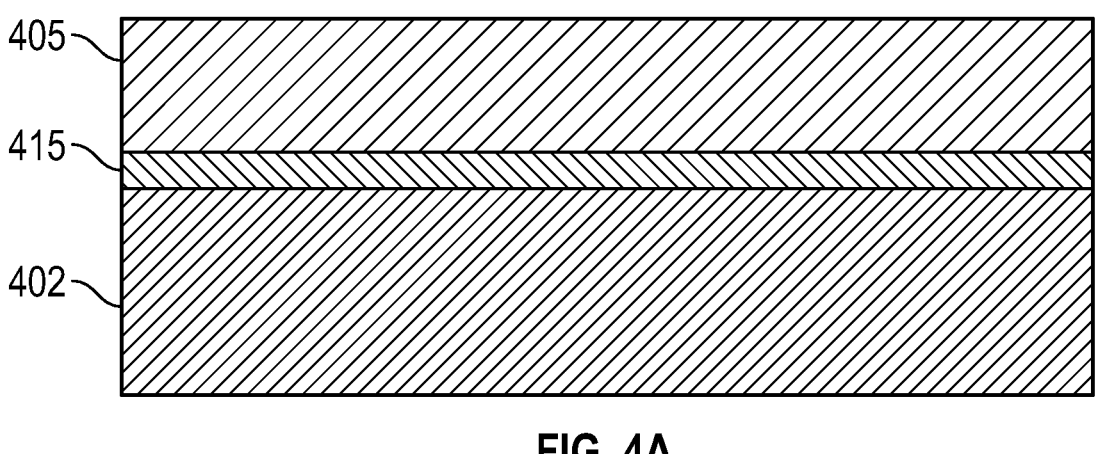
FIGS. 4A-4G illustrate an example of a microfabrication process to form a vibrating mesh membrane with an integrated piezoelectric film, in accordance with various embodiments.

FIGS. 4A-4G illustrate an embodiment of an example of a microfabrication process to form a vibrating mesh membrane with an integrated piezoelectric film. The microfabrication process can use techniques for forming integrated circuits such as silicon based integrated circuits or other integrated circuits that are constructed using such processes. FIG. 4A shows a structure after a device layer 405 has been formed on an electrically insulating layer 415 on a substrate 402, which is a bulk region. The device layer 405, insulating layer 415, and substrate 402 can be implemented using a silicon on insulator (SOI) wafer. Alternatively, the device layer 405 can be structured from material of one or more polymers. Such a polymer structure can be implemented on an insulating substrate, which can be realized as, but not limited to, an electrically insulating material on a bulk silicon structure.

Figure 4B:
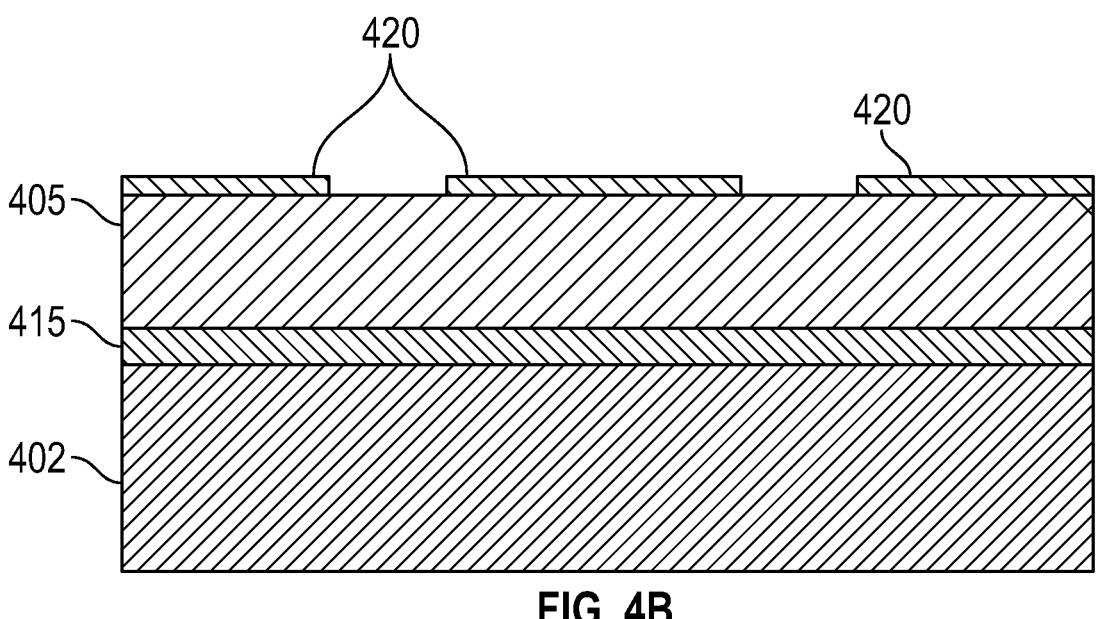
Figure 4C:
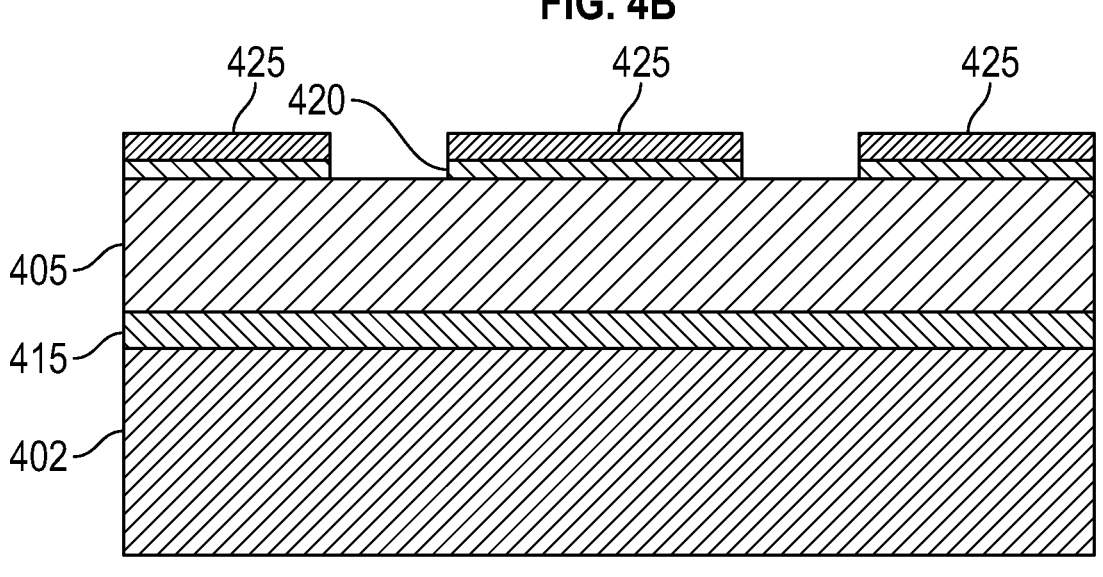

FIG. 4B shows the structure of FIG. 4A after a bottom electrode 420 has been deposited and patterned on device layer 405. The bottom electrode 420 can be titanium or other appropriate material to function as an electrode. FIG. 4C shows the structure of FIG. 4B after a layer of piezoelectric material 425 has been deposited and patterned on bottom electrode 420 such that at least a portion of the previous formed openings in bottom electrode 420 remains. The piezoelectric material 425 can be, but is not limited to, aluminum nitride, zinc oxide, PZT, or a polymer composite material.

Figure 4D:
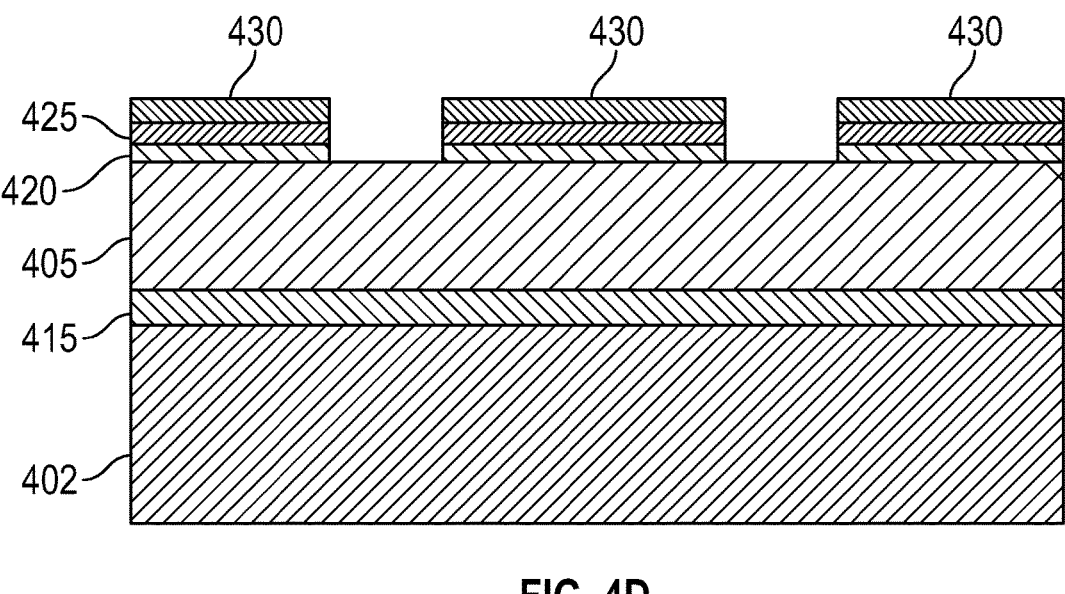

FIG. 4D shows the structure of FIG. 4C after a top electrode 430 has been deposited and patterned on piezoelectric material 425 such that at least a portion of the previous formed openings in bottom electrode 420 and piezoelectric material 425 remains. The top electrode 430 can be aluminum or other appropriate material to function as an electrode.

The openings through each of top electrode 430, piezoelectric material 425, and bottom electrode 420 can be formed using an etchant appropriate for each material layer after each layer is deposited. Alternatively, before any of these patterning processes, top electrode 430 can be deposited on piezoelectric material 425 that is deposited on bottom electrode 420 that is deposited on device layer 405. After these layers have been deposited to form a stack of layers, the stack can be subjected to one or more etchants in a patterning process to form the structure of FIG. 4D.

Figure 4E:
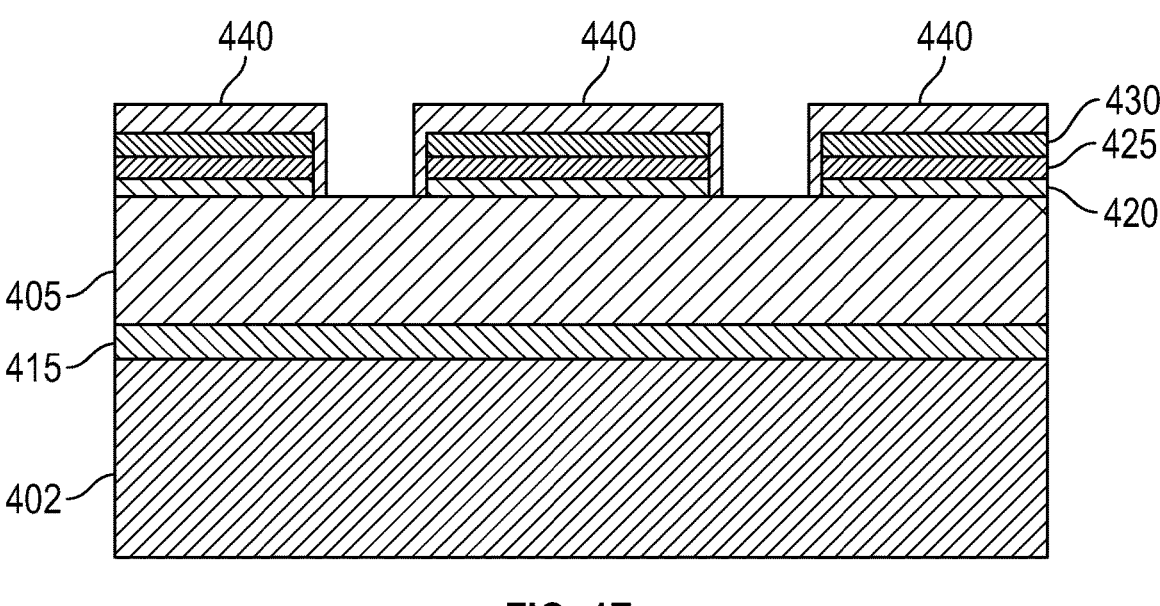

FIG. 4E shows the structure of FIG. 4D after a passivation layer 440 has been deposited and patterned on top electrode 430 such that at least a portion of the previous formed openings in top electrode 430, bottom electrode 420, and piezoelectric material 425 remains. Passivation layer 440 is a protective layer. Passivation layer 440 can be an electrically insulating layer that provides protection for the underlying layers. Passivation layer 440 can be deposited such that it covers the vertical sides of each of top electrode 430, piezoelectric material 425, bottom electrode 420 to device layer 405 to protect these regions in further processing.

Figure 4F:
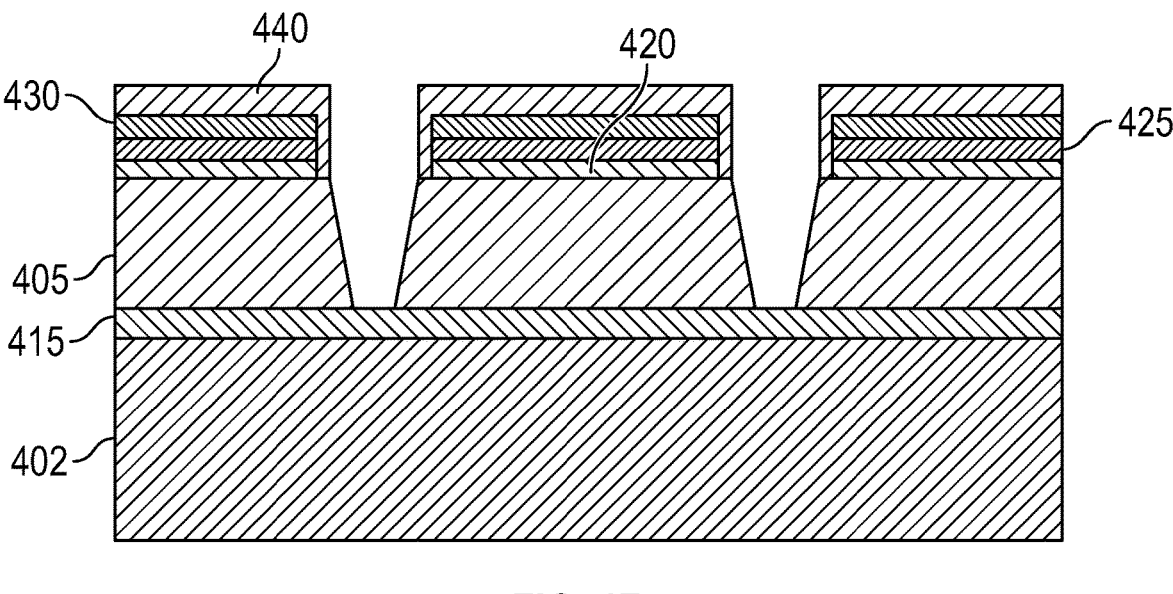
Figure 4G:
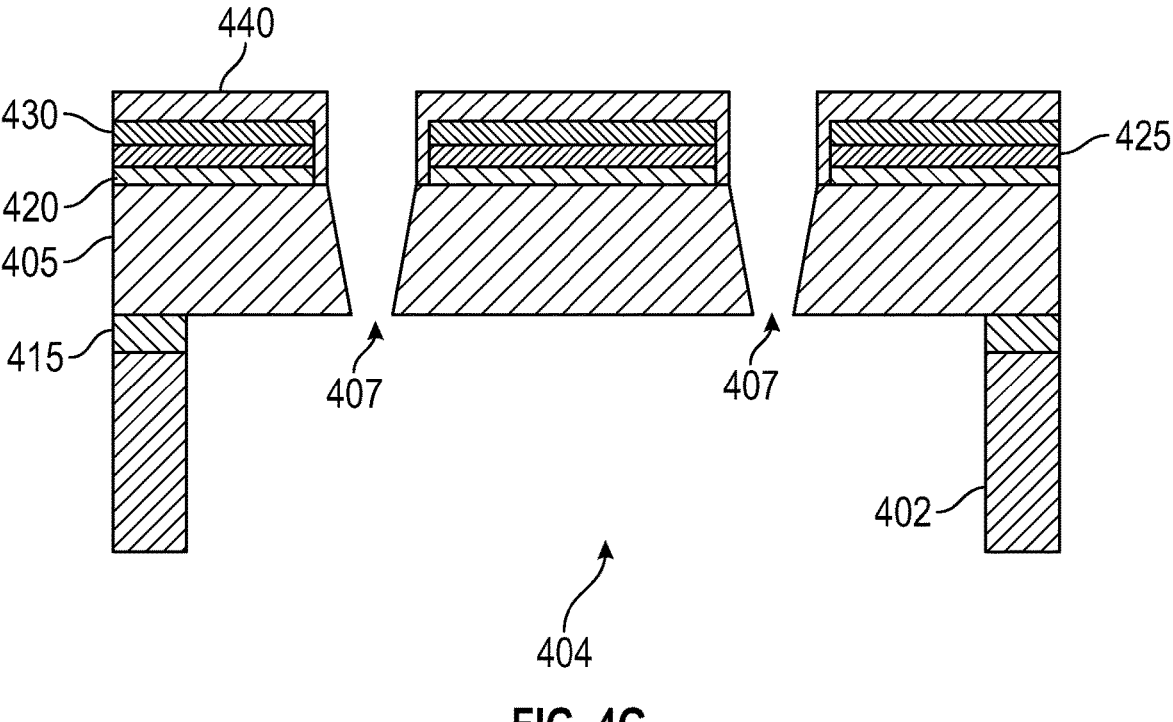

FIG. 4F shows the structure of FIG. 4E after an etchant has been applied to fabricate holes vertically through device layer 405 to insulating layer 415. The etch can be a wet etch of device layer 405, which can provide holes through device layer 405. FIG. 4G shows the structure of FIG. 4F after an etchant has been applied to create holes 407 in insulating layer 415 and an opening 404 in bulk substrate 402 to which holes 407 provide entrances. The etching process of insulating layer 415 and bulk substrate 402 can be a multiple stage process. The etching process can include a dry etch of bulk substrate 402. Bulk substrate 402 can be a region of bulk silicon, bulk polymer, or other appropriate bulk material.

The example fabrication process of FIGS. 4A-4G can provide an integrated mesh, which can function as a vibrating mesh, that can be integrated into a number of structures in a variety of applications. Such an integrated mesh can be implemented in an atomizer. The example fabrication process can include any of the manufacturing processes discussed herein within respect to integrated manufacturing such as those used in integrated circuit technology.

Figure 5A:
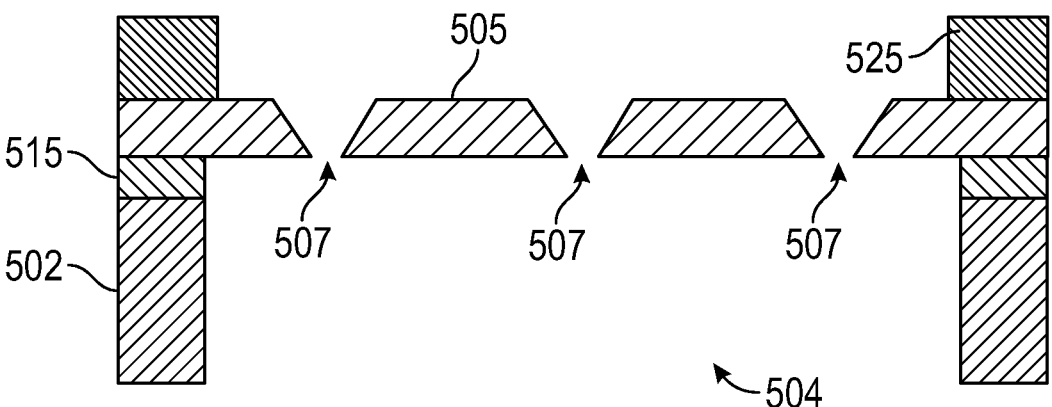
FIGS. 5A and 5B show a structure having a ring shaped piezoelectric film and electrode, forming a piezoelectric stack, which is on the outside of a mesh membrane, in accordance with various embodiments.
Figure 5B:
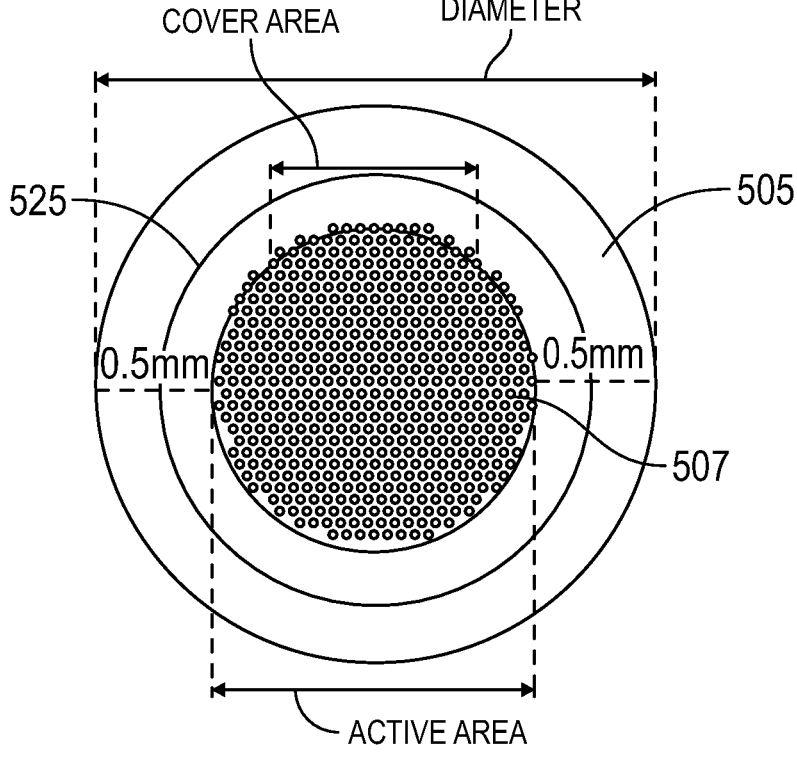

FIGS. 5A and 5B show a structure having a ring shaped piezoelectric film and electrode, forming a piezoelectric stack 525, which is on the outside of the mesh membrane 505. FIG. 5A is a cross-sectional view showing mesh membrane 505 having holes 507 providing entrances to opening 504 in an insulating region 515 and bulk substrate region 502. FIG. 5B is a top view of outer ring of piezoelectric material and electrode 525 with respect to mesh membrane 505 and holes 507. This arrangement produces lateral strain of the piezoelectric film to generate vertical displacement of the membrane 505. This provides the same output or results from the membrane 505 but uses a different piezoelectric mode. Use of a ring shaped electrode can make manufacturing or microfabrication of these devices much simpler. With the piezoelectric ring on the membrane rather than on the outside, the piezoelectric and electrode materials are to be selected to be compatible with etching techniques, which may include more detailed processing. Incompatibilities can lead to cracks or delamination of the piezoelectric material or the electrode material. By having the materials on the outside of the membrane, issues with potential delamination and crack formation of the piezoelectric material may be avoided. This structure allows use of a wider range of piezoelectric materials and electrode materials.

Figure 5C:
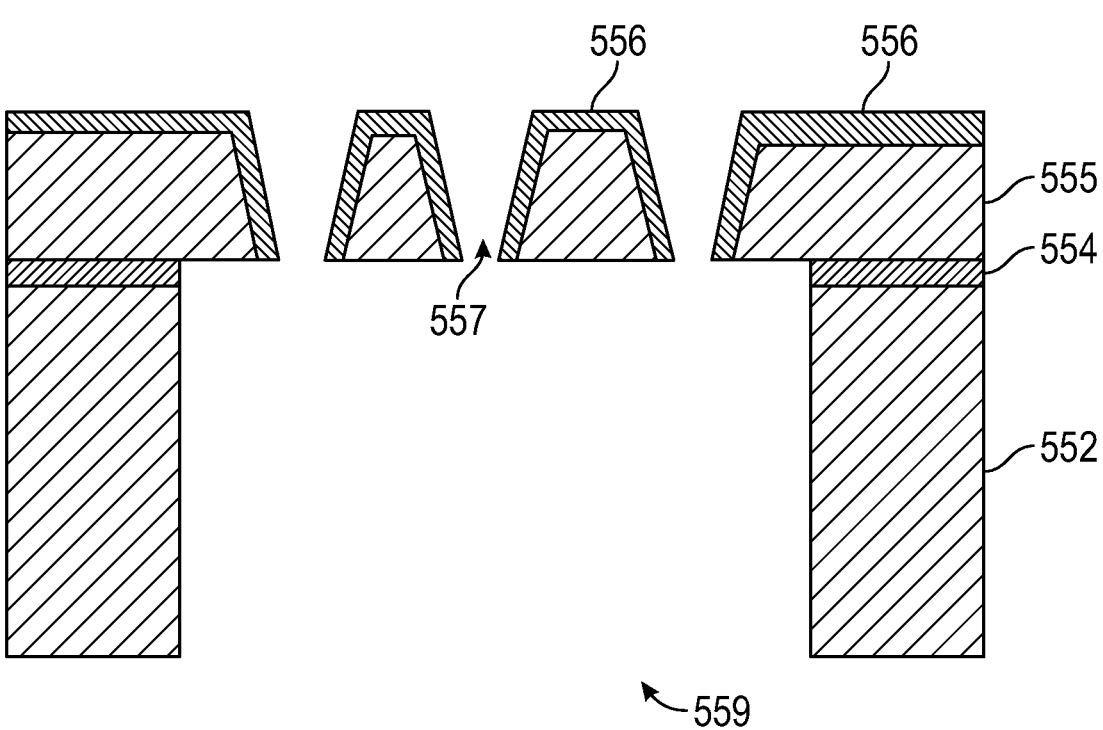
FIGS. 5C and 5D show a structure having a ring actuator and a base mesh membrane having a coating that prevents liquid to be dispensed from contacting the base mesh membrane, in accordance with various embodiments.
Figure 5D:
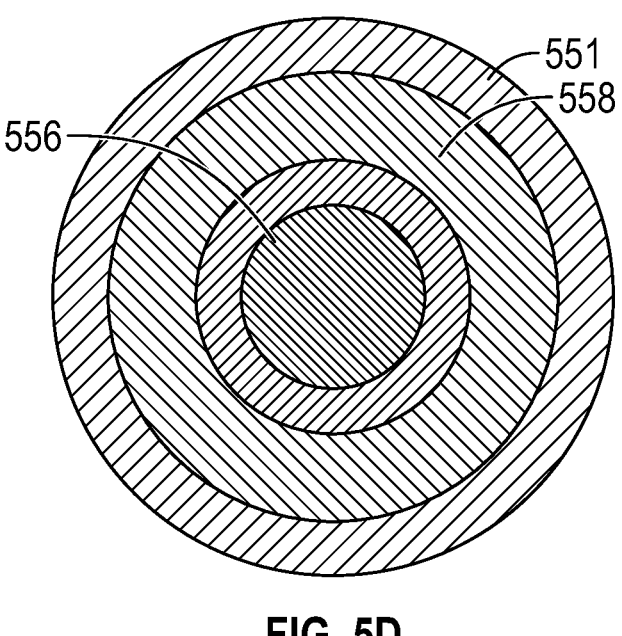
Figure 13:
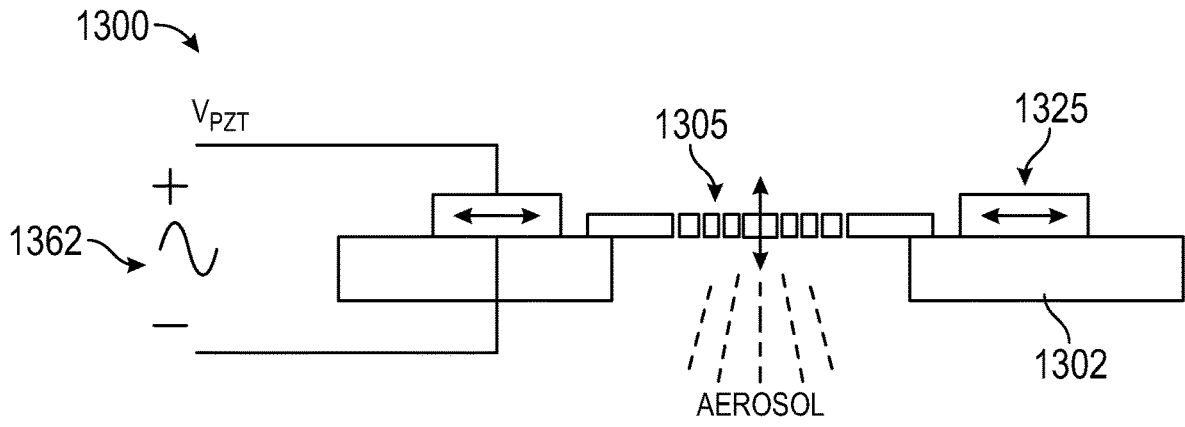
FIG. 13 illustrates an example operation principle that can be used with a vibrating mesh, in accordance with various embodiments.
Figure 14:
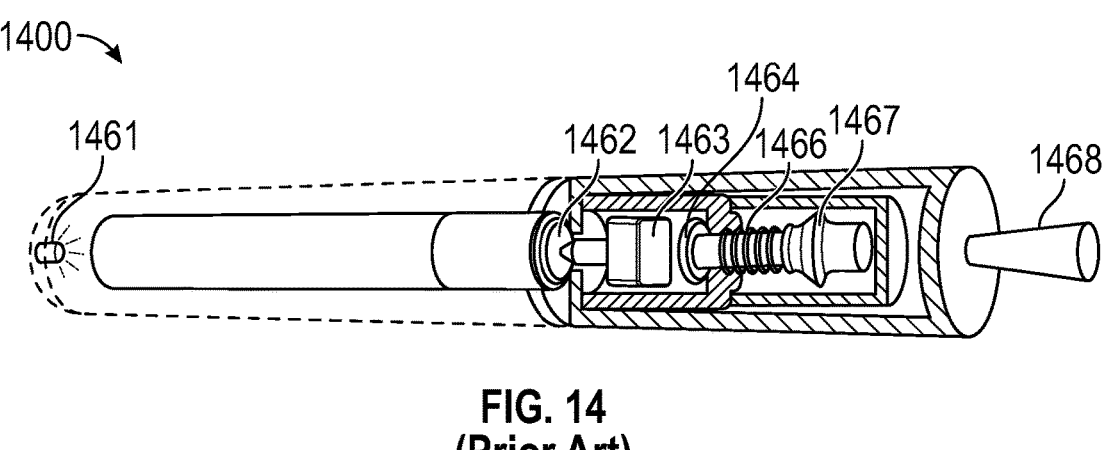
FIG. 14 illustrates a traditional e-cigarette.

FIGS. 5C and 5D show a structure having a ring actuator 558 and a base mesh membrane 555 having a coating 556 that prevents liquid to be dispensed from contacting base mesh membrane 555. The coating can be a coating of Parylene, which is a biocompatible polymer that is approved by the Food and Drug Administration (FDA). Parylene can be deposited using chemical vapor techniques that are compatible with microfabrication techniques. This is particularly useful in an e-cig device where it is desired that particles from the membrane are not to be inhaled. In addition, Parylene can be chemically modified to be hydrophobic or hydrophilic. FIG. 5C is a cross-sectional view showing base mesh membrane 555 having holes 557 providing entrances to opening 559 in an insulating region 554 and bulk substrate region 552. FIG. 5D is a top view of ring actuator 558 mounted on a holder 551 and coating 556. Ring actuator 558 can be a piezoelectric material such as but not limited to PZT. The device of FIGS. 5C-5D can be operated similar to the operation shown in FIG. 13.

Figures 6A, 6B:
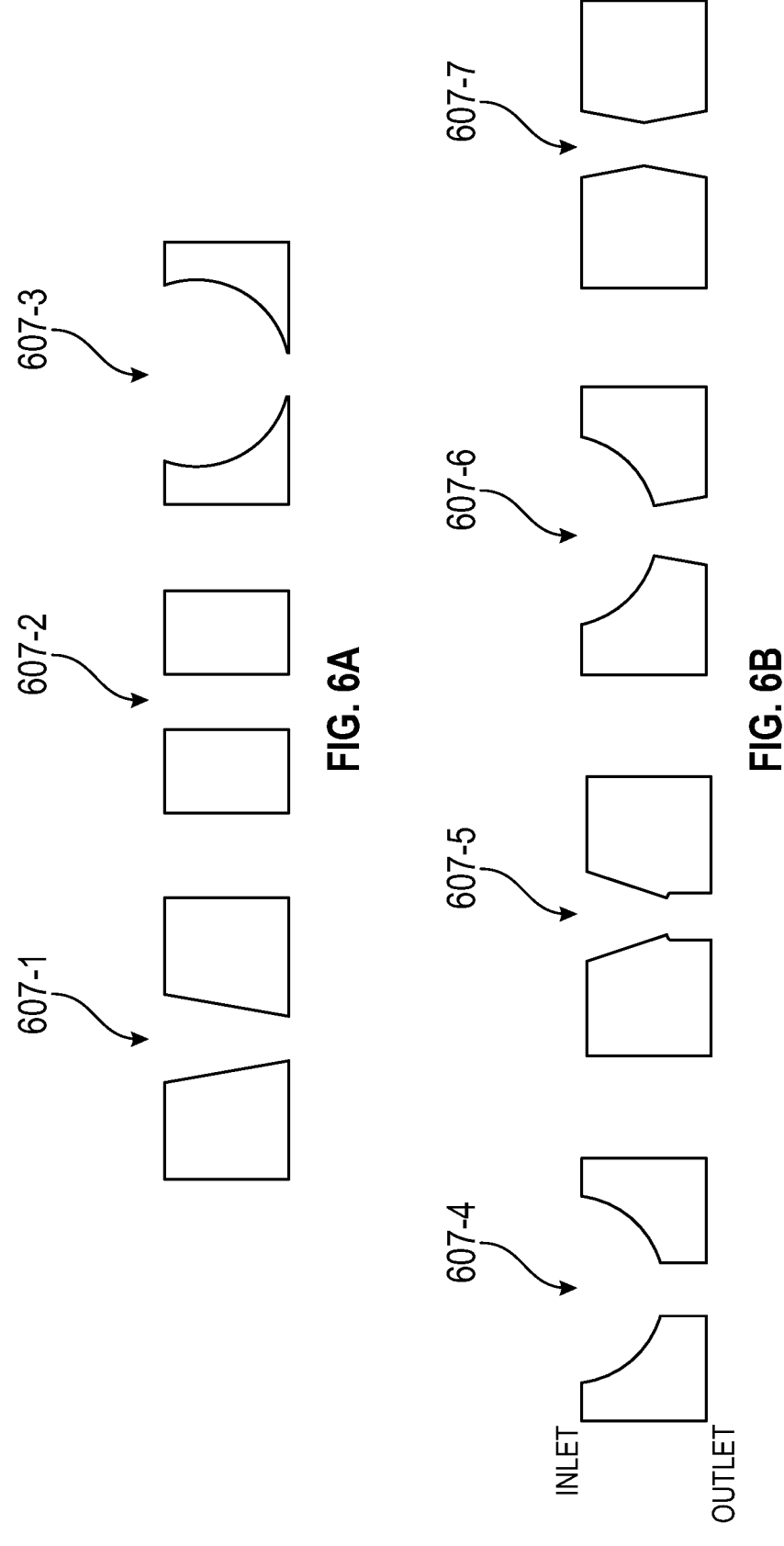
FIGS. 6A-6B illustrate example hole shapes that can be implemented in a mesh membrane, in accordance with various embodiments.

FIGS. 6A-6B illustrate embodiments of example hole shapes that can be implemented in a mesh membrane. FIG. 6A shows a pyramidal shape 607-1, a straight shape 607-2, and a circular shape 607-3. FIG. 6B illustrate embodiments of example hole shapes 607-4, 607-5, 607-6, and 607-7 from combination of methods, where such combination of methods can include combination of methods that generated the example hole shapes of FIG. 6A. The methods of generating holes can include using one or more etching processes based on the materials in the structure. Show in FIG. 6B are inlets and outlets for the hole shapes.

Figure 7A:
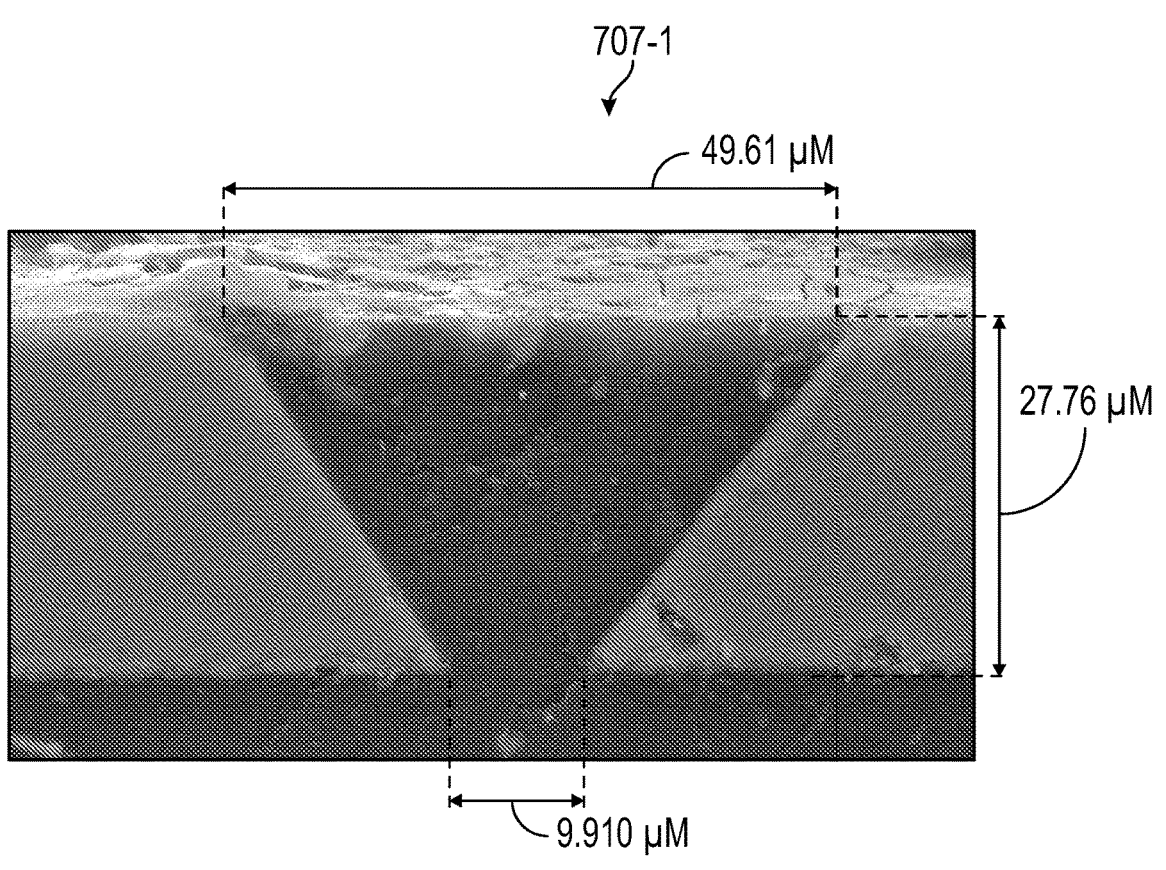
FIG. 7A is a cross-sectional scanning electron microscope image of an example hole shape, in accordance with various embodiments.
Figure 7B:
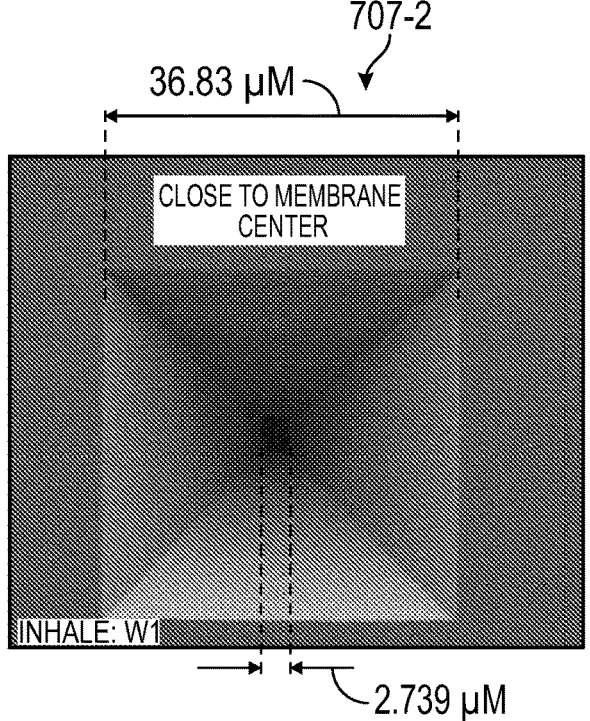
FIG. 7B is a top view of a hole shape corresponding to the hole shape of FIG. 7A, in accordance with various embodiments.

FIG. 7A is a cross-sectional scanning electron microscope (SEM) image of an embodiment of an example hole shape. FIG. 7B is a top view of an embodiment of an example hole shape corresponding to the example hole shape of FIG. 7A.

Figure 8A:
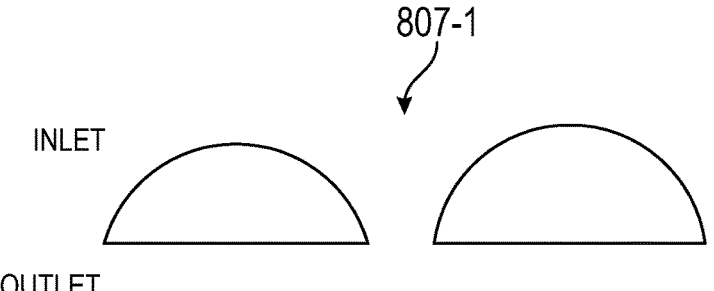
FIG. 8A illustrates an example hourglass shape having hole, in accordance with various embodiments.
Figure 8B:
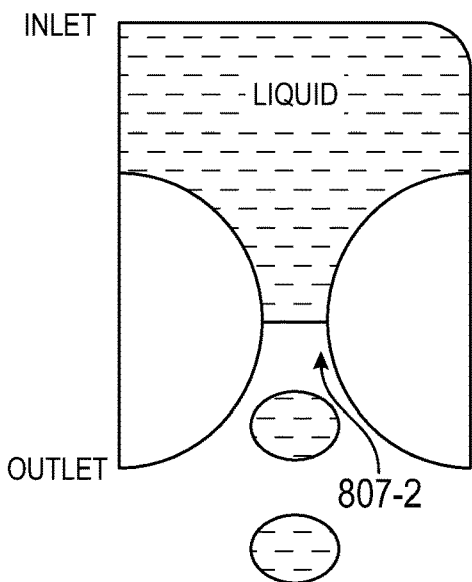
FIG. 8B illustrates an example of a liquid input to a hourglass shape structure having hole, in accordance with various embodiments.

FIG. 8A illustrates an embodiment of an example hourglass shape having hole 807-1. The hourglass shape can be a polymer hourglass shape. FIG. 8B illustrates an embodiment of an example of a liquid input to a hourglass shape structure having hole 807-2, which can be a polymer hourglass shape structure.

Figure 9:
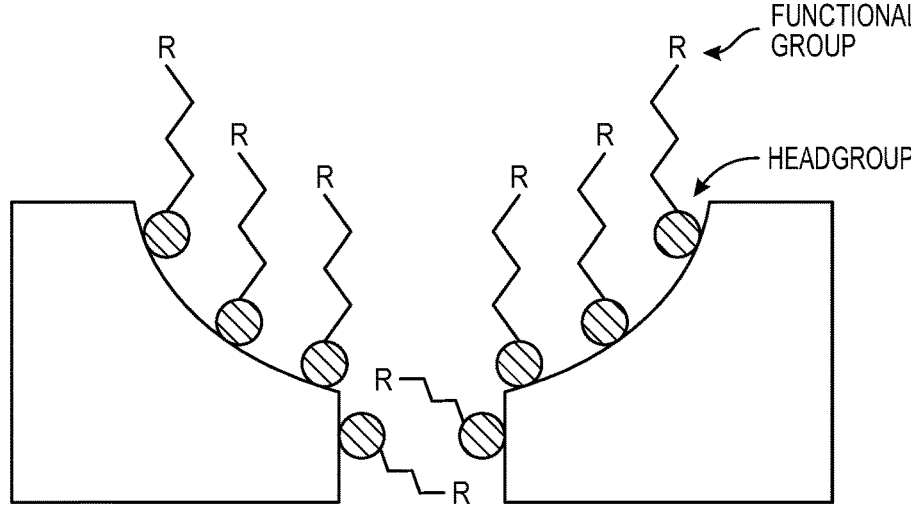
FIG. 9 illustrates an example surface hydrophobicity image, in accordance with various embodiments.

FIG. 9 illustrates an embodiment of an example surface hydrophobicity image. Shown in FIG. 9 are headgroups attaching to a surface that forms an opening in a mesh membrane. A headgroup is a bulky part of a molecule, which can have one or more functional groups that are attached to a relatively long aliphatic tail or backbone. Functional groups can be applied through numerous methods including wet chemistry processing as well as dry plasma or atomic layer deposition, which can be applied using standard microfabrication methods to produce superhydrophobic coatings. The hydrophobicity of the hole surface can affect the droplet size and how much force is required to push a liquid through the hole.

Figure 10A:
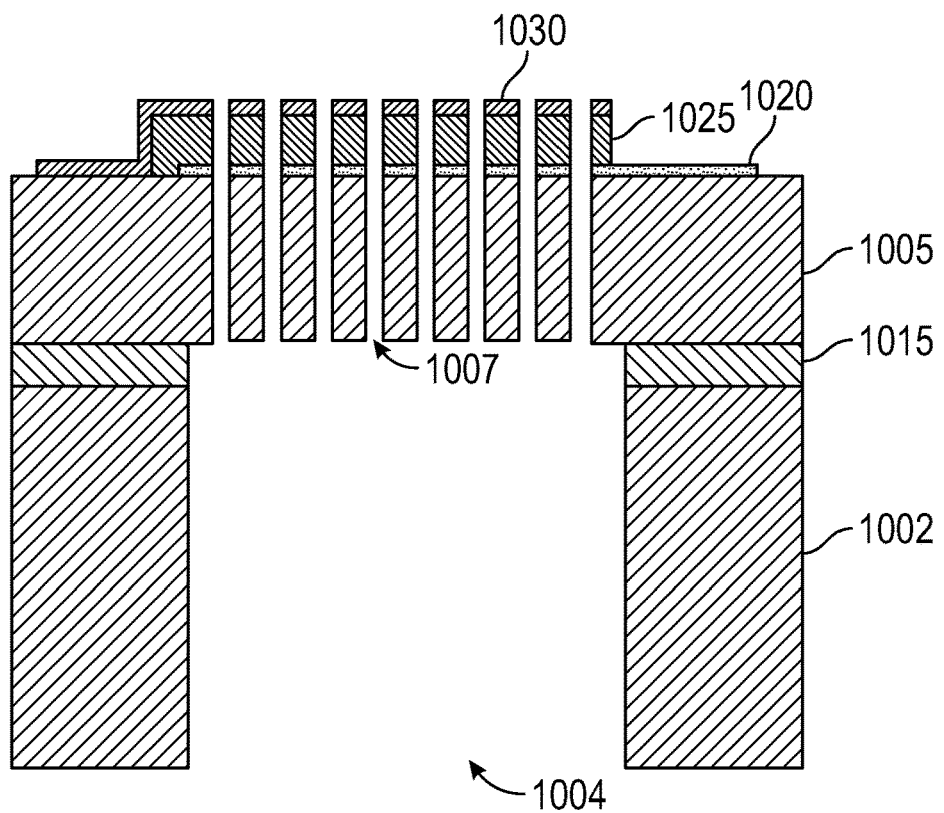
FIGS. 10A-10B illustrate an example device having a mesh membrane, where the device is arranged without microfluidic chambers, in accordance with various embodiments.
Figure 10B:
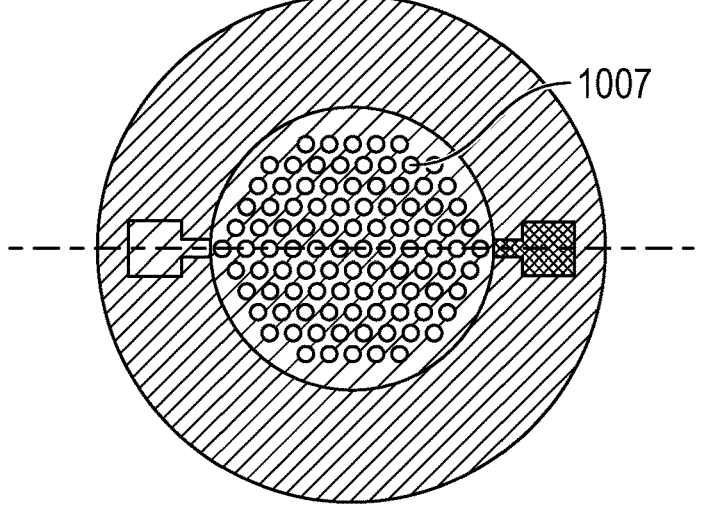

FIGS. 10A-10B illustrate an embodiment of an example device having a mesh membrane 1005, where the device is arranged without microfluidic chambers. FIG. 10A is a cross-sectional view showing a bulk substrate 1002, which can be bulk silicon or other appropriate bulk material. Disposed on bulk substrate 1002 is an insulating layer 1015 separating bulk substrate 1002 from mesh membrane 1005. A first electrode 1020 is disposed on mesh membrane 1005, where first electrode 1020 is separated from a second electrode 1030 by a piezoelectric film 1025. A number of holes 1007 are arranged through mesh membrane 1005, providing entrances to an opening 1004 in bulk substrate 1002 and insulating layer 1015. Holes 1007 can extend from above second electrode 1030 through the stacks formed by second electrode 1030, piezoelectric film 1025, bottom electrode 1020, and mesh membrane 1005 to opening 1004. FIG. 10B shows a top view of FIG. 10A showing the arrangement of holes 1007.

Figure 11A:
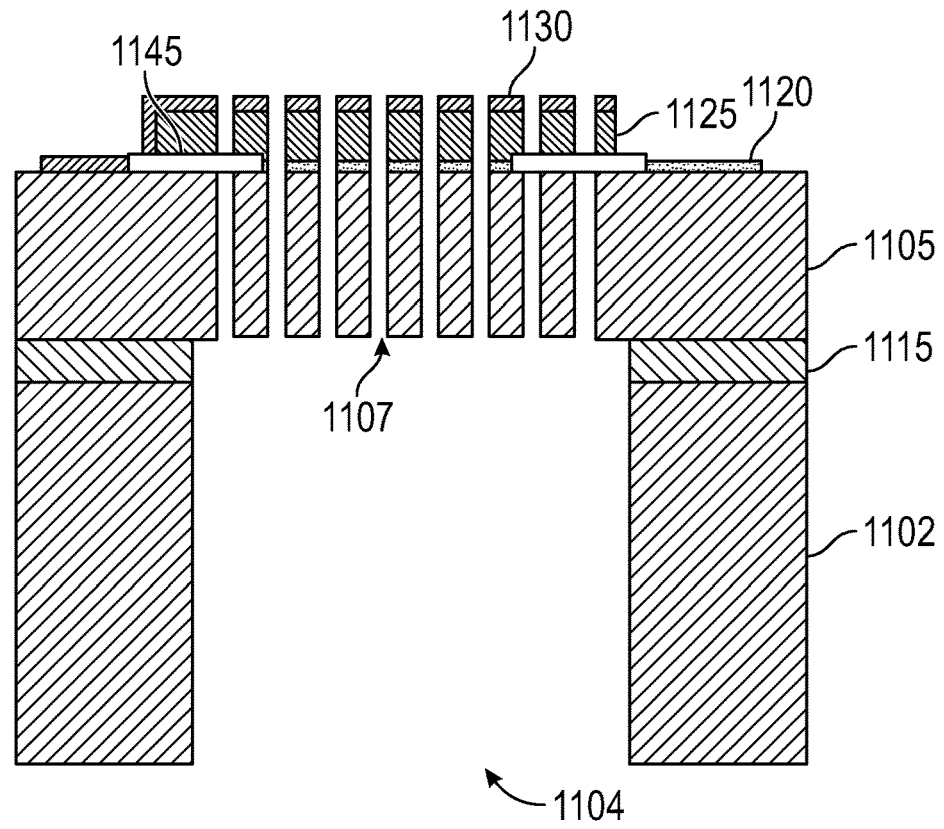
FIGS. 11A-11B illustrate an example device having a mesh membrane, where the device includes integrated pressure sensors, in accordance with various embodiments.
Figure 11B:
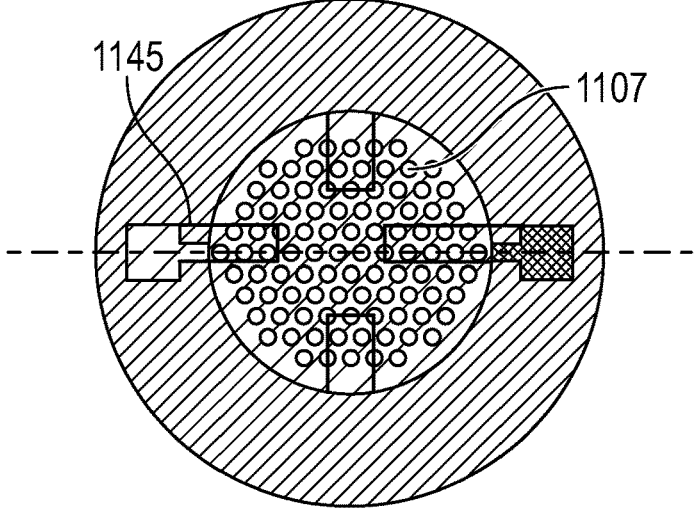
Figure 12A:
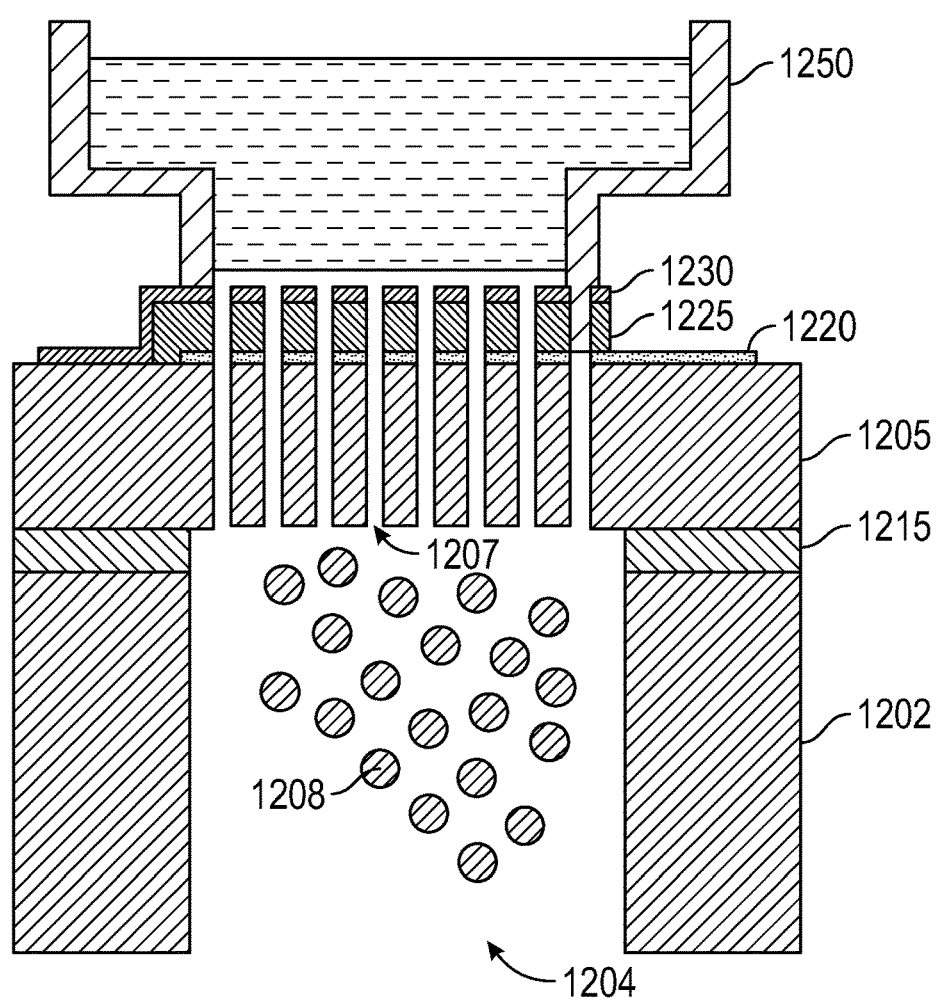
FIGS. 12A-12B illustrate an example device having a mesh membrane with microfluidic chambers above a mesh membrane, in accordance with various embodiments.
Figure 12B:
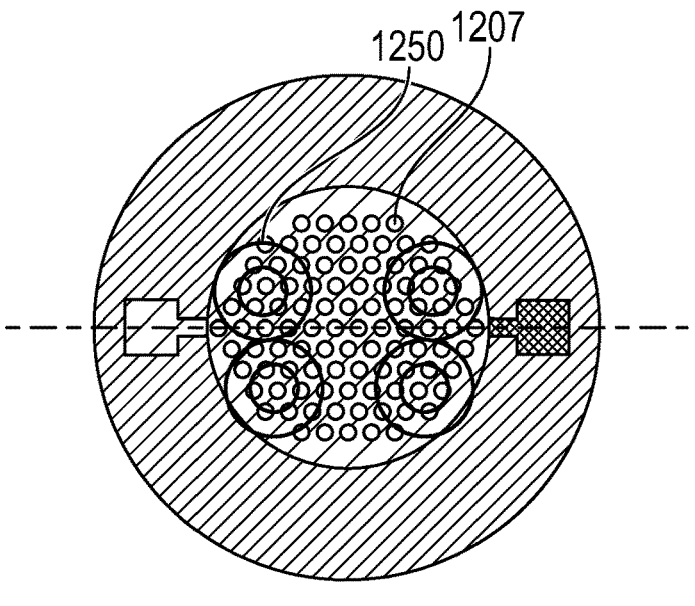

FIGS. 11A-11B illustrate an embodiment of an example device having a mesh membrane 1105, where the device includes integrated pressure sensors 1145. The device is shown without having microfluidic chambers. FIG. 11A is a cross-sectional view showing a bulk substrate 1102, which can be bulk silicon or other appropriate bulk material. Disposed on bulk substrate 1102 is an insulating layer 1115 separating bulk substrate 1102 from mesh membrane 1105. A first electrode 1120 is disposed on mesh membrane 1105, where first electrode 1120 is separated from a second electrode 1130 by a piezoelectric film 1125. A number of holes 1107 are arranged through mesh membrane 1105, providing entrances to an opening 1104 in bulk substrate 1102 and insulating layer 1115. Integrated pressure sensors 1145 can be arranged on mesh membrane 1105 over a number of holes 1107. Holes 1107 can extend from above second electrode 1130 through the stacks formed by second electrode 1130, piezoelectric film 1125, bottom electrode 1120, and mesh membrane 1105 to opening 1104. FIG. 11B shows a top view of FIG. 11A showing the arrangement of holes 1107.

FIGS. 12A-12B illustrates an embodiment of an example device having a mesh membrane 1205 with microfluidic chambers 1250 above mesh membrane 1205. FIG. 12A shows a cross-sectional view showing a bulk substrate 1202, which can be bulk silicon or other appropriate bulk material. Disposed on bulk substrate 1202 is an insulating layer 1215 separating bulk substrate 1202 from mesh membrane 1205. A first electrode 1220 is disposed on mesh membrane 1205, where first electrode 1220 is separated from a second electrode 1230 by a piezoelectric film 1225. A number of holes 1207 are arranged through mesh membrane 1205, providing entrances to an opening 1204 in bulk substrate 1202 and insulating layer 1215. Holes 1207 can extend from above second electrode 1230 through the stacks formed by second electrode 1230, piezoelectric film 1225, bottom electrode 1220, and mesh membrane 1205 to opening 1204. Microfluidic chamber 1250 is disposed above mesh membrane 1205 such that holes 1007 provide entrances to opening 1204 from microfluidic chamber 1250. Particles 1208 flow into opening 1004 from liquid in microfluidic chamber 1250 through holes 1007. The flow of particles 1208 can be controlled by a signal between first electrode 1220 and second electrode 1230 to actuate piezoelectric film 1225 to cause mesh membrane to vibrate. FIG. 12B shows a top view of FIG. 12A showing an of arrangement of microfluidic chambers 1250 and holes 1207.

In various embodiments, methods of creating aerosols vaping devices, such as but not limited to electronic cigarettes, and inhaled drug delivery can be implemented for portable applications. Such methods can be based on a vibrating mesh membrane, along with methods of manufacturing the mesh membrane. This technology can provide uniform control of droplet sizes, which can eliminate the ultrafine particles that are potentially a health risk. In electronic cigarettes, the health risk can be associated with particles entering the blood stream.

The mesh membrane can include a thin film membrane with holes etched into the membrane, where the vibration can be created by using a thin film piezoelectric material. Voltage applied to the piezoelectric film causes the membrane to resonate, which forces the liquid through the holes creating an aerosol.

In embodiments, as taught herein, of fabricating an atomizer, can use monolithic manufacturing techniques for creating these devices. Such microfabrication techniques can integrate one or more thin film piezoelectric materials and one or more pressure sensors. This technology has the capability of controlling droplet size with high uniformity, which can eliminate ultrafine particle formation caused from vaping. The monolithic microfabrication process integrates the piezoelectric material, and it allows for unique hole shape and dimensions that can be used to control droplet formation. In addition, the microfabrication allows for alterations in hydrophobicity using deposited monolayers and the addition of microfluidic chambers. Further, since the manufacturing technique uses batch fabrication processing, pressure sensors can be monolithically integrated so that the portable device can turn on during inhalation, which causes a change in pressure.

In various embodiments, microfabrication techniques can be used to monolithically manufacture vibrating mesh devices with integrated thin film piezoelectric materials and integrate the device into a portable electronic-cigarette device. Microfabrication techniques allows one to make modifications to issues mentioned herein to control droplet size uniformity and flow rate. A portable atomizer can replace the current heating vaping devices with a vibrating mesh device that is able to control droplet size and flow rate with higher uniformity.

Current vaping devices require battery, microprocessor, sensor, heating element, cartridge, and nozzle. Using microfabrication techniques allows fabrication of an atomizing device with reduced number of components by integrating multiple components onto the atomizer. In various embodiments, a sensor, an atomizer, and a nozzle can be monolithically manufactured. With the piezoelectric material used being compatible with current CMOS techniques, a microprocessor could also be included in a vaping device, thus reducing the abovementioned components from six to three. The integrated structure can allow for precise control of droplet sizes for different applications.

Vibrating mesh atomizer technology, as taught herein, does not require heating to create an aerosol like current vaping technology. However, heating elements could be integrated into the atomizer using metal micro-heaters if desired. However, heating liquid in vaping has been linked to possible health risks by creating compounds of toxic chemicals.

Sensors, such as but not limited to strain gauges, can be integrated into the membrane structure, as shown in FIGS. 11A and 11B, using metal, doped silicon, a layer of polysilicon, or other conductive material. The sensor, like current sensors in electronic cigarettes, can be used to detect inhalation by the user. Once a pressure change is detected, a microprocessor of a vaping device structured using a vibration mesh membrane, as taught herein, can be triggered, where an alternating current (AC) voltage can be applied to the piezoelectric film of the vaping device, which causes the membrane to resonate at its resonant frequency, forcing the liquid through the mesh (nozzle) creating a stream of aerosol. See FIG. 15 for example.

FIG. 13 illustrates an example operation principle that can be used with a vibrating mesh for various embodiments. For an atomizer 1300, a voltage source 1362 generates a voltage, VPZT, that can be applied to a PZT ring 1325 on a holder/support 1303, providing a vibration to a mesh 1305. An aerosol is generated from a liquid above (not shown) mesh 1305.

FIG. 14 illustrates a traditional e-cigarette 1400. The components of the e-cigarette 1400 include a LED 1461 , a battery 1462, a microprocessor 1463, a sensor 1464, a heater 1466, a cartridge 1467, which outputs steam 1468 as an aspiration. The LED 1461 lights up when the smoker draws on the e-cigarette 1400. Microprocessor 1463 controls heater 1466 and LED light 1461. Sensor 1464 detects when the smoker inhales. Heater 1466 vaporizes liquid and nicotine in cartridge 1467, cartridge 1467 holds nicotine dissolved in propylene glycol.

Figure 15:
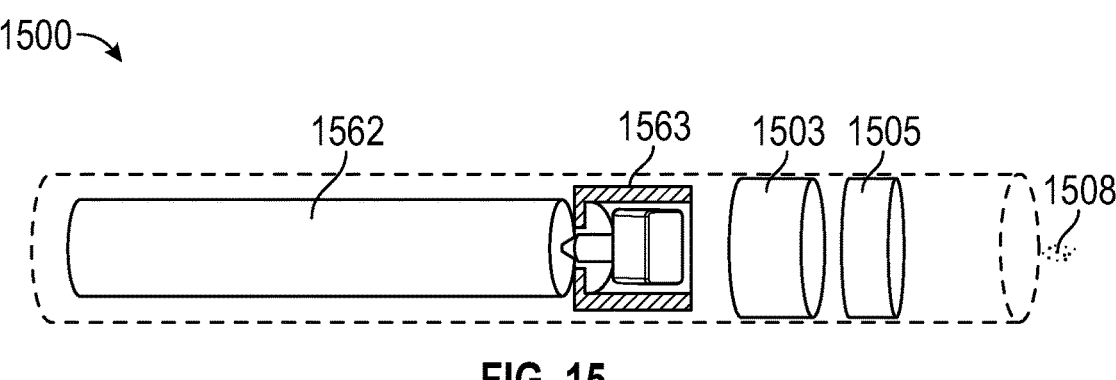
FIG. 15 illustrates an example e-cigarette having a vibrating mesh atomizer, in accordance with various embodiments.

FIG. 15 illustrates an embodiment of an example e-cigarette 1500 having a vibrating mesh atomizer. The components of e-cigarette 1500 can include a battery 1562, a microprocessor 1563, a liquid cartridge 1503, and a vibrating mesh atomizer 1505, with sensor, which outputs an aerosol 1505. The vibrating mesh atomizer 1505 with sensor can be implemented in accordance with the teachings herein. Such portable vibrating mesh atomizers can be implemented in applications other than e-cigarettes.

In various embodiments, an apparatus can comprise a bulk substrate with an insulating layer on top of the bulk substrate, with an opening in the bulk substrate and insulating layer, and a mesh membrane integrated with the insulating layer and disposed on and contacting the insulating layer with the mesh membrane extending over the opening. The mesh membrane can have multiple holes arranged to provide entry paths to the opening. A first conductive layer is integrated with the mesh membrane and disposed on and contacting the mesh membrane. A piezoelectric film can be integrated with the first conductive layer and disposed on and contacting the first conductive layer. A second conductive layer can be integrated with the piezoelectric film and disposed on and contacting the piezoelectric film, with the first conductive layer, the piezoelectric film, and the second conductive layer arranged to operatively vibrate the mesh membrane in response to a signal provided between the first conductive layer and the second conductive layer. The first conductive layer, the piezoelectric film, and the second conductive layer can be arranged as part of a vibrating mesh atomizer.

The holes in the mesh membrane can be arranged to extend through the first conductive layer, the piezoelectric film, and the second conductive layer. In another embodiment, the first conductive layer, the piezoelectric film, and the second conductive layer can be structured having a ring shape and are disposed on an outside of the mesh membrane. The holes can have a shape selected from a set of multiple shapes, where the set of multiple shapes can include an hourglass shape. One or more surfaces defining one or more holes can have attached monolayers that make the surface more hydrophilic or more hydrophobic.

Variations of such an apparatus or similar apparatus can include a number of different embodiments that may be combined depending on the application of such apparatus and/or the architecture of systems in which such apparatus are implemented. The apparatus can include material of the mesh membrane to include a number of materials. The mesh membrane can include silicon. The mesh membrane can include a polymer. Variations can include the apparatus having an integrated pressure sensor coupled to the mesh membrane. Variations of such an apparatus or similar apparatus can include a microfluidic chamber disposed above the mesh membrane such that the holes provide entrances to the opening from the microfluidic chamber. Variations of such an apparatus or similar apparatus can include a thin film coating to prevent liquid to substrate interaction. For example, coatings, such as but not limited to Parylene, can be deposed on the surface of a membrane and nozzle to prevent liquid to membrane surface interaction. Variations can include the apparatus being a vaping device. The vaping device can be an e-cigarette. Variations can include the apparatus being a liquid drug delivery system.

The apparatus, similar apparatus, or variations of such an apparatus can be operated by applying a signal between the first conductive layer and the second conductive layer of the apparatus to vibrate the mesh membrane in response to the application of the signal. Operating the apparatus can include operating a vaping device. The vaping device can be an e-cigarette. The operating method can include outputting an aerosol in response to a sensor detecting user activity of the e-cigarette. The method of operation can include controlling the outputting of the aerosol using a microprocessor of the e-cigarette with the microprocessor arranged to receive a sensor signal from the sensor integrated with the e-cigarette.

FIG. 16 is a flow diagram of features of a method 1600 of forming an apparatus having a mesh membrane. At 1610, a mesh membrane is formed integrating the mesh membrane with an insulating layer and disposed on and contacting the insulating layer, with the insulating layer disposed on top of a bulk substrate. At 1620, a first conductive layer is formed integrating the first conductive layer with the mesh membrane and disposed on and contacting the mesh membrane. At 1630, a piezoelectric film is formed integrating the piezoelectric film with the first conductive layer and disposed on and contacting the first conductive layer. At 1640, a second conductive layer is formed integrating the second conductive layer with the piezoelectric film and disposed on and contacting the piezoelectric film. At 1650, multiple holes are formed in the mesh membrane. At 1660, an opening is formed in the bulk substrate and insulating layer such that the mesh membrane extends over the opening with the multiple holes in the mesh membrane arranged to provide entry paths to the opening.

Variations of method 1600 or methods similar to method 1600 can include a number of different embodiments that may be combined depending on the application of such methods and/or the architecture of systems in which such methods are implemented. Such methods can include coupling a voltage source to the first conductive layer and the second conductive layer to operatively vibrate the mesh membrane in response to a signal from the voltage source provided between the first conductive layer and the second conductive layer. Variations can include forming the holes in the mesh membrane to extend through the first conductive layer, the piezoelectric film, and the second conductive layer. Variations can include forming the first conductive layer, the piezoelectric film, and the second conductive layer having a ring shape disposed on an outside of the mesh membrane.

Variations can include the mesh membrane can include silicon. The mesh membrane can include a polymer. Variations can include forming the holes having a shape selected from a set of multiple shapes. Forming the shape of the holes can be using a combination of etching processes associated with forming the multiple shapes. Hydrophobicity of a surface of a hole of the multiple holes can be controlled. Controlling hydrophobicity of the surface can include attaching one or more monolayers to the surface. Forming multiple holes can include forming the multiple holes to control droplet size, droplet shape, and force to push liquid out of the multiple holes.

Variations of method 1600 or methods similar to method 1600 can include arranging the first conductive layer, the piezoelectric film, and the second conductive layer as part of a vibrating mesh atomizer. Variations can include integrating a pressure sensor coupled to the mesh membrane. Variations can include forming a microfluidic chamber disposed above the mesh membrane such that the holes provide entrances to the opening from the microfluidic chamber.

Variations of method 1600 or methods similar to method 1600 can include forming the apparatus to include forming a vaping device. Forming the vaping device can include forming an e-cigarette. Variations can include forming the apparatus to include forming a liquid drug delivery system.

The following are example embodiments of a monolithic microfabricated piezomems device and associated methods, in accordance with the teachings herein.

An example apparatus 1 can comprise: a bulk substrate with an insulating layer on top of the bulk substrate, with an opening in the bulk substrate and insulating layer; a mesh membrane integrated with the insulating layer and disposed on and contacting the insulating layer with the mesh membrane extending over the opening, the mesh membrane having multiple holes arranged to provide entry paths to the opening; a first conductive layer integrated with the mesh membrane and disposed on and contacting the mesh membrane; a piezoelectric film integrated with the first conductive layer and disposed on and contacting the first conductive layer; and a second conductive layer integrated with the piezoelectric film and disposed on and contacting the piezoelectric film, with the first conductive layer, the piezoelectric film, and the second conductive layer arranged to operatively vibrate the mesh membrane in response to a signal provided between the first conductive layer and the second conductive layer.

An example apparatus 2 can include features of example apparatus 1 and can include the holes in the mesh membrane arranged to extend through the first conductive layer, the piezoelectric film, and the second conductive layer.

An example apparatus 3 can include features of any of the preceding example apparatus and can include the first conductive layer, the piezoelectric film, and the second conductive layer structured having a ring shape and are disposed on an outside of the mesh membrane.

An example apparatus 4 can include features of any of the preceding example apparatus and can include the holes having a shape selected from a set of multiple shapes.

An example apparatus 5 can include features of any of the preceding example apparatus and can include the set of multiple shapes including an hourglass shape.

An example apparatus 6 can include features of any of the preceding example apparatus and can include one or more surfaces defining one or more holes have attached monolayers that make the surface more hydrophilic or more hydrophobic.

An example apparatus 7 can include features of any of the preceding example apparatus and can include the mesh membrane includes silicon.

An example apparatus 8 can include features of any of the preceding example apparatus and can include the mesh membrane includes a polymer.

An example apparatus 9 can include features of any of the preceding example apparatus and can include the first conductive layer, the piezoelectric film, and the second conductive layer being arranged as part of a vibrating mesh atomizer.

An example apparatus 10 can include features of any of the preceding example apparatus and can include an integrated pressure sensor coupled to the mesh membrane.

An example apparatus 11 can include features of any of the preceding example apparatus and can include a microfluidic chamber disposed above the mesh membrane such that the holes provide entrances to the opening from the microfluidic chamber.

An example apparatus 12 can include features of any of the preceding example apparatus and can include the apparatus including a thin film coating to prevent liquid to substrate interaction.

An example apparatus 13 can include features of any of the preceding example apparatus and can include the apparatus being a vaping device.

An example apparatus 14 can include features of any of the preceding example apparatus and can include the vaping device being an e-cigarette.

An example apparatus 15 can include features of any of the preceding example apparatus and can include the apparatus being a liquid drug delivery system.

An example method 1 of forming an apparatus having a mesh membrane can comprise: forming a mesh membrane integrated with an insulating layer and disposed on and contacting the insulating layer, with the insulating layer on top of a bulk substrate; forming a first conductive layer integrated with the mesh membrane and disposed on and contacting the mesh membrane; forming a piezoelectric film integrated with the first conductive layer and disposed on and contacting the first conductive layer; forming a second conductive layer integrated with the piezoelectric film and disposed on and contacting the piezoelectric film; forming multiple holes in the mesh membrane; and forming an opening in the bulk substrate and insulating layer such that the mesh membrane extends over the opening with the multiple holes in the mesh membrane arranged to provide entry paths to the opening.

An example method 2 of forming an apparatus having a mesh membrane can include features of example method 1 and can include coupling a voltage source to the first conductive layer and the second conductive layer to operatively vibrate the mesh membrane in response to a signal from the voltage source provided between the first conductive layer and the second conductive layer.

An example method 3 of forming an apparatus having a mesh membrane can include features of any of the preceding example methods and can include forming the holes in the mesh membrane to extend through the first conductive layer, the piezoelectric film, and the second conductive layer.

An example method 4 of forming an apparatus having a mesh membrane can include features of any of the preceding example methods and can include forming the first conductive layer, the piezoelectric film, and the second conductive layer having a ring shape disposed on an outside of the mesh membrane.

An example method 5 of forming an apparatus having a mesh membrane can include features of any of the preceding example methods and can include forming the holes having a shape selected from a set of multiple shapes.

An example method 6 of forming an apparatus having a mesh membrane can include features of any of the preceding example methods and can include forming the holes having a shape using a combination of etching processes associated with forming the multiple shapes.

An example method 7 of forming an apparatus having a mesh membrane can include features of any of the preceding example methods and can include controlling hydrophobicity of a surface of a hole of the multiple holes.

An example method 8 of forming an apparatus having a mesh membrane can include features of any of the preceding example methods and can include controlling hydrophobicity of the surface including attaching one or more monolayers to the surface.

An example method 9 of forming an apparatus having a mesh membrane can include features of any of the preceding example methods and can include the mesh membrane including silicon.

An example method 10 of forming an apparatus having a mesh membrane can include features of any of the preceding example methods and can include the mesh membrane including a polymer.

An example method 11 of forming an apparatus having a mesh membrane can include features of any of the preceding example methods and can include arranging the first conductive layer, the piezoelectric film, and the second conductive layer as part of a vibrating mesh atomizer.

An example method 12 of forming an apparatus having a mesh membrane can include features of any of the preceding example methods and can include integrating a pressure sensor coupled to the mesh membrane.

An example method 13 of forming an apparatus having a mesh membrane can include features of any of the preceding example methods and can include forming a microfluidic chamber disposed above the mesh membrane such that the holes provide entrances to the opening from the microfluidic chamber.

An example method 14 of forming an apparatus having a mesh membrane can include features of any of the preceding example methods and can include forming the apparatus including forming a vaping device.

An example method 15 of forming an apparatus having a mesh membrane can include features of any of the preceding example methods and can include forming the vaping device to include forming an e-cigarette.

An example method 16 of forming an apparatus having a mesh membrane can include features of any of the preceding example methods and can include forming the apparatus includes forming a liquid drug delivery system.

An example method 17 of forming an apparatus having a mesh membrane can include features of any of the preceding example methods and can include forming multiple holes including forming the multiple holes to control droplet size, droplet shape, and force to push liquid out of the multiple holes.

An example method 18 of forming an apparatus having a mesh membrane can include features of any of the preceding example methods of forming an apparatus having a mesh membrane and can include performing functions associated with any features of example apparatus 1-15 and any features of example apparatus associated with the figures herein.

An example method 1 of operating an apparatus having a mesh membrane can comprise: applying a signal between a first conductive layer and a second conductive layer of the apparatus to vibrate the mesh membrane in response to the application of the signal, the apparatus including: a bulk substrate with an insulating layer on top of the bulk substrate with an opening in the bulk substrate and insulating layer; the mesh membrane integrated with the insulating layer and disposed on and contacting the insulating layer with the mesh membrane extending over the opening, the mesh membrane having multiple holes arranged to provide entry paths to the opening; the first conductive layer integrated with the mesh membrane and disposed on and contacting the mesh membrane; a piezoelectric film integrated with the first conductive layer and disposed on and contacting the first conductive layer; and the second conductive layer integrated with the piezoelectric film and disposed on and contacting the piezoelectric film, the piezoelectric film arranged with the first conductive layer and the second conductive layer to operatively vibrate the mesh.

An example method 2 of operating an apparatus having a mesh membrane can include features of example method 1 and can include operating the apparatus to include operating a vaping device.

An example method 3 of operating an apparatus having a mesh membrane can include features of any of the preceding example methods and can include the vaping device being an e-cigarette.

An example method 4 of operating an apparatus having a mesh membrane can include features of any of the preceding example methods and can include outputting an aerosol in response to a sensor detecting user activity of the e-cigarette.

An example method 5 of operating an apparatus having a mesh membrane can include features of any of the preceding example methods and can include controlling the outputting of the aerosol using a microprocessor of the e-cigarette with the microprocessor arranged to receive a sensor signal from the sensor integrated with the e-cigarette.

Although specific embodiments have been illustrated and described herein, it will be appreciated by those of ordinary skill in the art that any arrangement that is calculated to achieve the same purpose may be substituted for the specific embodiments shown. Upon studying the disclosure, it will be apparent to those skilled in the art that various modifications and variations can be made in the devices and methods of various embodiments of the invention. Various embodiments can use permutations and/or combinations of embodiments described herein. Other embodiments will be apparent to those skilled in the art from consideration of the specification and practice of the embodiments disclosed herein. It is to be understood that the above description is intended to be illustrative, and not restrictive, and that the phraseology or terminology employed herein is for the purpose of description.

What is claimed is:

1. An apparatus comprising:
   a bulk substrate with an insulating layer on top of the bulk substrate, with an opening in the bulk substrate and insulating layer;
   a mesh membrane integrated with the insulating layer and disposed on and contacting the insulating layer with the mesh membrane extending over the opening, the mesh membrane being a flat mesh membrane having multiple holes arranged as a set of nozzles to provide entry paths to the opening, the set including nozzles of different shapes, each nozzle having an inlet and an outlet, the outlet having a non-circular shape and arranged to provide an entry path to the opening in the bulk substrate and insulating layer, the nozzles of different shapes to dispense droplets through the outlets with selected viscosities based on respective shapes of the nozzles, the nozzles including a nozzle having a shape between the inlet of the nozzle and the outlet of the nozzle that includes a combination of a flat tapered surface extending along a path between the inlet and the outlet of the nozzle and a non-flat tapered surface extending along the path between the inlet and the outlet of the nozzle;
   a first conductive layer integrated with the mesh membrane and disposed on and contacting the mesh membrane;
   a piezoelectric film integrated with the first conductive layer and disposed on and contacting the first conductive layer; and a second conductive layer integrated with the piezoelectric film and disposed on and contacting the piezoelectric film, with the first conductive layer, the piezoelectric film, and the second conductive layer arranged to operatively vibrate the mesh membrane in response to a signal provided between the first conductive layer and the second conductive layer.

2. The apparatus of claim 1, wherein the holes in the mesh membrane are arranged to extend through the first conductive layer, the piezoelectric film, and the second conductive layer.

3. The apparatus of claim 1, wherein the first conductive layer, the piezoelectric film, and the second conductive layer are structured having a ring shape and are disposed on an outside of the mesh membrane.

4. The apparatus of claim 1, wherein a top surface of the mesh membrane, opposite the outlets, and surfaces of the holes are coated with a biocompatible polymer that is hydrophobic or hydrophilic.

5. The apparatus of claim 1, wherein the different shapes include an hourglass shape or a wine glass shape.

6. The apparatus of claim 1, wherein one or more surfaces defining one or more holes have attached monolayers that make the surface more hydrophilic or more hydrophobic.

7. The apparatus of claim 1, wherein the mesh membrane includes silicon.

8. The apparatus of claim 1, wherein the mesh membrane includes a polymer having piezoelectric nanoparticles incorporated within the polymer.

9. The apparatus of claim 1, wherein the first conductive layer, the piezoelectric film, and the second conductive layer are arranged as part of a vibrating mesh atomizer.

10. The apparatus of claim 1, wherein the apparatus includes an integrated pressure sensor arranged on top of and contacting the mesh membrane over a number of holes of the mesh membrane.

11. The apparatus of claim 1, wherein the apparatus includes a thin film coating to prevent liquid to substrate interaction.

12. The apparatus of claim 1, wherein the apparatus is a vaping device.

13. The apparatus of claim 12, wherein the vaping device is an electronic cigarette having a sensor, to detect inhalation, monolithically integrated with an atomizer on a single the bulk substrate, the atomizer provided by the mesh membrane, the first conductive layer, the piezoelectric film, and the second conductive layer integrated on the bulk substrate, the bulk substrate being a single substrate.

14. The apparatus of claim 1, wherein the apparatus is a liquid drug delivery system.

15. An apparatus comprising:
a bulk substrate with an insulating layer on top of the bulk substrate, with an opening in the bulk substrate and insulating layer;
a mesh membrane integrated with the insulating layer and disposed on and contacting the insulating layer with the mesh membrane extending over the opening, the mesh membrane having multiple holes arranged as a set of nozzles to provide entry paths to the opening, the set including nozzles of different shapes, each nozzle having an outlet opening arranged to provide an entry path to the opening in the bulk substrate and insulating layer;
a first conductive layer integrated with the mesh membrane and disposed on and contacting the mesh membrane;

a piezoelectric film integrated with the first conductive layer and disposed on and contacting the first conductive layer;
a second conductive layer integrated with the piezoelectric film and disposed on and contacting the piezoelectric film, with the first conductive layer, the piezoelectric film, and the second conductive layer arranged to operatively vibrate the mesh membrane in response to a signal provided between the first conductive layer and the second conductive layer; and
multiple microfluidic chambers disposed above the mesh membrane such that different ones of the multiple microfluidic chambers, arranged to hold different fluids, are aligned with different sets of holes of the mesh membrane such that the different sets of the holes provide different entrances to the opening from the multiple microfluidic chambers.

16. A method of forming an apparatus having a mesh membrane, the method comprising:
forming a mesh membrane as a flat mesh membrane integrated with an insulating layer and disposed on and contacting the insulating layer, with the insulating layer on top of a bulk substrate;
forming a first conductive layer integrated with the mesh membrane and disposed on and contacting the mesh membrane;
forming a piezoelectric film integrated with the first conductive layer and disposed on and contacting the first conductive layer;
forming a second conductive layer integrated with the piezoelectric film and disposed on and contacting the piezoelectric film;
forming multiple holes in the mesh membrane arranged as a set of nozzles, each nozzle having an inlet and an outlet, the set including nozzles of different shapes, by wet etching, dry etching, or a combination of wet and dry etching the mesh membrane to configure the nozzles of different shapes having etched surfaces to dispense droplets through outlets with selected viscosities based on respective shapes of the nozzles; nozzles, the nozzles including a nozzle having an outlet with a non-circular shape and a shape between the inlet of the nozzle and the outlet of the nozzle that includes a combination of a flat tapered surface extending along a path between the inlet and the outlet of the nozzle and a non-flat tapered surface; surface extending along the path between the inlet and the outlet of the nozzle; and
forming an opening in the bulk substrate and insulating layer such that the mesh membrane extends over the opening with each nozzle outlet arranged to provide an entry path to the opening in the bulk substrate and insulating layer.

17. The method of claim 16, wherein the method includes coupling a voltage source to the first conductive layer and the second conductive layer to operatively vibrate the mesh membrane in response to a signal from the voltage source provided between the first conductive layer and the second conductive layer.

18. The method of claim 16, wherein the method includes forming the holes in the mesh membrane to extend through the first conductive layer, the piezoelectric film, and the second conductive layer.

19. The method of claim 16, wherein the method includes forming the first conductive layer, the piezoelectric film, and the second conductive layer having a ring shape disposed on an outside of the mesh membrane.

20. The method of claim 16, wherein the method includes modifying a top surface of the mesh membrane, opposite the outlets, and surfaces of the holes to be hydrophobic or hydrophilic.

21. The method of claim 16, wherein the method includes forming the different shapes using a combination of etching processes.

22. The method of claim 16, wherein the method includes controlling hydrophobicity of a surface of a hole of the multiple holes.

23. The method of claim 22, wherein controlling hydrophobicity of the surface includes attaching one or more monolayers to the surface.

24. The method of claim 16, wherein the mesh membrane includes silicon.

25. The method of claim 16, wherein the mesh membrane includes a polymer.

26. The method of claim 16, wherein the method includes arranging the first conductive layer, the piezoelectric film, and the second conductive layer as part of a vibrating mesh atomizer.

27. The method of claim 16, wherein the method includes integrating multiple pressure sensors arranged on top of and contacting the mesh membrane, each of the multiple pressure sensors arranged over a number of holes of the mesh membrane.

28. The method of claim 16, wherein forming the apparatus includes forming a vaping device.

29. The method of claim 28, wherein forming the vaping device includes forming an electronic cigarette including monolithically integrating a sensor, to detect inhalation, with an atomizer grown on the bulk substrate, the atomizer provided by the mesh membrane, the first conductive layer, the piezoelectric film, and the second conductive layer grown on the bulk substrate, the bulk substrate being a single substrate.

30. The method of claim 16, wherein forming the apparatus includes forming a liquid drug delivery system.

31. The method of claim 16, wherein forming multiple holes includes forming the multiple holes to control droplet size, droplet shape, and force to push liquid out of the multiple holes.

32. A method of forming an apparatus having a mesh membrane, the method comprising:

forming a mesh membrane integrated with an insulating layer and disposed on and contacting the insulating layer, with the insulating layer on top of a bulk substrate;

forming a first conductive layer integrated with the mesh membrane and disposed on and contacting the mesh membrane;

forming a piezoelectric film integrated with the first conductive layer and disposed on and contacting the first conductive layer;

forming a second conductive layer integrated with the piezoelectric film and disposed on and contacting the piezoelectric film;

forming multiple holes in the mesh membrane arranged as a set of nozzles, the set including nozzles of different shapes;

forming an opening in the bulk substrate and insulating layer such that the mesh membrane extends over the opening with each nozzle having an outlet opening arranged to provide an entry path to the opening in the bulk substrate and insulating layer; and forming multiple microfluidic chambers disposed above the mesh membrane such that different ones of the multiple microfluidic chambers, arranged to hold different fluids, are aligned with different sets of holes of the mesh membrane such that the different sets of the holes provide different entrances to the opening from the multiple microfluidic chambers.

33. A method of operating an apparatus having a mesh membrane, the method comprising:

applying a signal between a first conductive layer and a second conductive layer of the apparatus to vibrate the mesh membrane in response to the application of the signal, the apparatus including:

a bulk substrate with an insulating layer on top of the bulk substrate with an opening in the bulk substrate and insulating layer;

the mesh membrane integrated with the insulating layer and disposed on and contacting the insulating layer with the mesh membrane extending over the opening, the mesh membrane being a flat mesh membrane having multiple holes arranged as a set of nozzles to provide entry paths to the opening, the set including nozzles of different shapes, each nozzle having an inlet and an outlet, the outlet having a non-circular shape and arranged to provide an entry path to the opening in the bulk substrate and insulating layer, the nozzles of different shapes to dispense droplets through the outlets with selected viscosities based on respective shapes of the nozzles, the nozzles including a nozzle having a shape between the inlet of the nozzle and the outlet of the nozzle that includes a combination of a flat tapered surface extending along a path between the inlet and the outlet of the nozzle and a non-flat tapered surface extending along the path between the inlet and the outlet of the nozzle;

the first conductive layer integrated with the mesh membrane and disposed on and contacting the mesh membrane;

a piezoelectric film integrated with the first conductive layer and disposed on and contacting the first conductive layer; and the second conductive layer integrated with the piezoelectric film and disposed on and contacting the piezoelectric film, the piezoelectric film arranged with the first conductive layer and the second conductive layer to operatively vibrate the mesh.

34. The method of claim 33, wherein operating the apparatus includes operating a vaping device.

35. The method of claim 34, wherein the vaping device is an electronic cigarette having a sensor to detect inhalation, the sensor monolithically integrated with an atomizer on the bulk substrate, the atomizer provided by the mesh membrane, the first conductive layer, the piezoelectric film, and the second conductive layer integrated on the bulk substrate, the bulk substrate being a single substrate.

36. The method of claim 35, wherein the method includes outputting an aerosol in response to a sensor detecting user activity of the electronic cigarette.

37. The method of claim 36, wherein the method includes controlling the outputting of the aerosol using a microprocessor of the electronic cigarette with the microprocessor arranged to receive a sensor signal from a sensor integrated with the electronic cigarette.

* * * * *